US009670497B2

(12) United States Patent
Venter et al.

(10) Patent No.: US 9,670,497 B2
(45) Date of Patent: Jun. 6, 2017

(54) SYNTHETIC PROMOTER CONSTRUCT FOR TRANSGENE EXPRESSION

(71) Applicant: Azargen Biotechnologies (Pty) Ltd., Stellenbosch (ZA)

(72) Inventors: Mauritz Venter, Western Cape (ZA); Jacobus Petrus Zwiegelaar, Western Cape (ZA)

(73) Assignee: AZARGEN BIOTECHNOLOGIES (PTY) LTD., Cape Town (ZA)

(*) Notice: Subject to any disclaimer, the term of this patent is extended or adjusted under 35 U.S.C. 154(b) by 17 days.

(21) Appl. No.: 14/575,479

(22) Filed: Dec. 18, 2014

(65) Prior Publication Data

US 2015/0329869 A1    Nov. 19, 2015

(30) Foreign Application Priority Data

May 19, 2014    (ZA) .................................. 2014/03606

(51) Int. Cl.
*C12N 15/82*    (2006.01)
*C07K 14/785*    (2006.01)

(52) U.S. Cl.
CPC ........ *C12N 15/8216* (2013.01); *C07K 14/785* (2013.01); *C12N 15/8222* (2013.01); *C12N 15/8238* (2013.01); *C12N 15/8257* (2013.01); *C07K 2319/60* (2013.01)

(58) Field of Classification Search
None
See application file for complete search history.

(56) References Cited

U.S. PATENT DOCUMENTS

| | | | | |
|---|---|---|---|---|
| 6,031,075 A * | 2/2000 | Weaver | ................ | C07K 14/785 530/324 |
| 6,172,203 B1 | 1/2001 | Hager et al. | | |
| 7,405,074 B2 * | 7/2008 | Castle | ................ | C12N 15/8275 435/193 |
| 2006/0123515 A1 * | 6/2006 | Daniell | ................. | C07K 14/56 800/288 |
| 2012/0023627 A1 * | 1/2012 | Gampala | ............. | C12N 15/8216 800/300 |

FOREIGN PATENT DOCUMENTS

| | | |
|---|---|---|
| CN | 102229951 B | 6/2013 |
| WO | WO 03020899 A2 | 3/2003 |
| WO | WO 2008000445 A1 | 1/2008 |

OTHER PUBLICATIONS

Genbank Accession No. X15221. Apr. 24, 1991, *A. thaliana* 5' flanking region of cab2 gene and cab2 gene (partial) for chlorophyll a/b-binding protein.*

An. Integrated regulation of the photosynthetic gene family from *Arabidopsis thaliana* in transformed tobacco cells. Mol Gen Genet (1987) 207:210-216.*
Desai et al. Production of heterologous proteins in plants: strategies for optimal expression. Biotechnology Advances, 28 (2010), 427-435.*
Liu et al. Light-harvesting chlorophyll a/b-binding proteins, positively involved in abscisic acid signaling, require a transcription factor repressor, WRKY40, to balance their function. Journal of Experimental Botany, vol. 64, No. 18, pp. 5443-5456, 2013.*
Kim et al. A 20 nucleotide upstream element is essential for the nopaline synthase (nos) promoter activity. Plant Mol Biol. Jan. 1994;24(1):105-17.*
Benfey et al., Combinatorial and synergistic properties of CaMV 35S enhancer subdomains, EMBO Journal 9(6):1685-1696 (1990).
Benfey et al., The Cauliflower Mosaic Virus 35S Promoter: Combinatorial Regulation of Transcription in Plants, Science 250:959-966 (Nov. 1990).
Bhullar et al., Strategies for Development of Functionally Equivalent Promoters with Minimum Sequence Homology for Transgene Expression in Plants: cis-Elements in a Novel DNA Context Versus Domain Swapping, Plant Physiol 132:988-998 (Jun. 2003).
Bhullar et al., Functional analysis of the cauliflower mosaic virus 35S promoter: re-evaluation of the role of subdomains B5, B4, and B2 in promoter activity, Plant Biotechnol Journal 5:686-708 (2007).
Higo et al., Plant cis-acting regulatory DNA elements (Place) database:1999, Nucleic Acids Research 27(1):297-300 (1999).
Horsch et al., A simple and general method for transferring genes into plants, Science 227(4691):1229-1231 (1985).
Lescot et al., PlantCARE, a database of plant cis-acting regulatory elements and a portal to tools for in silico analysis of promoter sequences, Nucleic Acids Research 30(1):325-327 (2002).
Mattanovich et al., Efficient transformation of *Agrobacterium* spp. by electroporation, Nucleic Acids Research 17(16):6747 (1989).
Mitsuhara et al., Efficient Promoter Cassettes for Enhanced Expression of Foreign Genes in Dicotyledonous and Monocotyledonous Plants, Plant Cell Physiol 37(1):49-59 (1996).
Pryhuber, G, Regulation and Function of Pulmonary Surfactant Protein B, Molecular Genetics and Metabolism 64:217-228 (1998).
Venter M, Synthetic promoters: genetic control through cis engineering, Trends in Plant Sci. 12(3):118-124 (2007).
Venter and Botha, Plant Developmental Biology-Biotechnological Perspectives vol. 2 (eds Pua and Davey) Chapter 20 "Synthetic Promoter Engineering", pp. 393-408 (Springer) (2010).
Almlen et al., "Synthetic Surfactant Based on Analogues of SP-B and SP-C Is Superior to Single-Peptide Surfactants in Ventilated Premature Rabbits", Neonatology, 98:91-99 (2010).
Berlec and Strukelj, "Current state and recent advances in biopharmaceutical production in *Escherichia coli*, yeasts and mammalian cells", J. Ind. Microbiol. Biotechnol, 40:257-274 (2013).
Blanco et al., "An update on clinical surfactant preparations and respiratory disease", Biotecnologia Aplicada, 29(2):53-59 (2012).

(Continued)

*Primary Examiner* — Cynthia Collins
(74) *Attorney, Agent, or Firm* — Wenderoth, Lind & Ponack, L.L.P.

(57) ABSTRACT

The invention is directed to synthetic promoter constructs for enhanced transgene expression in plants and to expression cassettes comprising the synthetic promoter constructs. The expression cassettes may include various elements for improved expression, stability of the expressed protein or efficient purification of the expressed protein, including signal sequences, protease cleavage sites for release of the target protein, trafficking peptides for trafficking of the expressed protein to various plant compartments, and/or various tags. The invention further relates to methods of expression of transgenic proteins in plants with the use of the synthetic promoter constructs and expression cassettes.

23 Claims, 3 Drawing Sheets

(56) References Cited

OTHER PUBLICATIONS

Clark and Clark, "The genetics of neonatal respiratory disease", Seminars in Fetal & Neonatal Medicine, 10:271-282 (2005).
Cockshutt and Possmayer, "Metabolism of Surfactant Lipids and Proteins in the Developing Lung", Pulmonary Surfactant from molecular biology to clinical practice, Elsevier Science Publishers B.V., Chapter 16, pp. 339-377, (1992).
Creuwels et al., "The Pulmonary Surfactant System: Biochemical and Clinical Aspects", Lung, 175:1-39 (1997).
Desai et al., "Production of heterologous proteins in plants: Strategies for optimal expression", Biotechnol. Advances, 28(4):427-435, (Jul. 1, 2010).
Drugmand et al., "Insect cells as factories for biomanufacturing", Biotechnology Advances, 30:1140-1157 (2012).
Engle, William A., "Surfactant-Replacement Therapy for Respiratory Distress in the Preterm and Term Neonate", Pediatrics, 121(2):419-432 (Feb. 2008).
Finer, Neil N., "Surfactant use for neonatal lung injury: beyond respiratory distress syndrome", Paediatric Respiratory Reviews, 5(Suppl A):5289-5297, (2004).
GenBank [online] Apr. 24, 1991 "*A. thaliana* 5' flanking region of cab2 gene and cab2 gene (partial) or chlorophyll a/b-binding protein" [retrieved on Apr. 26, 2016] GenBank. X15221.
Gleave, Andrew P., "A versatile binary vector system with a T-DNA organizational structure conducive to efficient integration of cloned DNA into the plant genome", Plant Molecular Biology, 20:1203-1207 (1992).
Goerke et al., Pulmonary surfactant functions and molecular composition, Biochimica et Biophysica Acta, Molecular Basis of Disease, Amsterdam, NL, 408(2-3):79-89 (Nov. 19, 1998).
Griese, M., "Pulmonary surfactant in health and human lung diseases: state of the art", Eur Respir J. 13:1455-1476 (1999).
Guttentag and Foster, "Update in Surfactant Therapy", NeoReviews, 12(11):c625-c634 (Nov. 2011).
Halliday, HL, "Surfactants: past, present and future", Journal of Perinatology, 28:S47-S56 (2008).
Hataaja and Hallman, "Surfactant proteins as genetic determinants of multifactorial pulmonary diseases", Trends in Molecular Medicine, Ann med 34:324-333 (2002).
Huang et al., "Industrial production of recombinant therapeutics in *Escherichia coli* and its recent advancements", J Ind Microbiol Biotechnol., 39:383-399 (2012).
Jobe, Alan H., "Pulmonary Surfactant Therapy", The New England Journal of Medicine, Drug Therapy, 328(12):861-868 (Mar. 1993).
Jordan and Donn, "Lucinactant for the prevention of respiratory distress syndrome in premature infants", Expert Review of Clinical Pharmacology, 6.2, p. 115:1-12 (Mar. 2013).
Kim et al., "CHO cells in biotechnology for production of recombinant proteins: current state and further potential", Appl Microbiol Biotechnol., 93:917-930 (2012).
Lico, Chiara et al., *The use of plants for the production of therapeutic human peptides*, Plant Cell Reports, 31(3):439-451 (Mar. 1, 2012).
Lukovic et al., "Production and characterization of recombinant forms of human pulmonary surfactant protein C (SP-C): Structure and surface activity", Biochimica et Biophysica Acta, 1758:509-518 (2006).
Lusuardi, et al., "Role of Surfactant in Chronic Obstructive Pulmonary Disease: Therapeutic Implications", Respiration, 59(suppl 1):28-32 (1992).
Ma and Ma, "The Role of Surfactant in Respiratory Distress Syndrome", The Open Respiratory Medicine Journal, 6:44-53 (2012).
Mallory, Jr., G.B., "Surfactant proteins: role in lung physiology and disease in early life", Paediatric Respiratory Reviews, 2:151-158 (2001).
Mattanovich, et al., Recombinant Protein Production in Yeasts, Chapter 17, Recombinant Gene Expression: Reviews and Protocols, Third Edition, Methods in Molecular Biology, vol. 824, Springer Science Business Media, LLC (2012) (33 pages).
Mingarro et al., "Synthetic Pulmonary Surfactant Preparations: New Developments and Future Trends", Current Medicinal Chemistry, 15:393-403 (2008).
Mitra, et al., "Structural and functional analyses of *Arabidopsis thaliana* chlorophyll a/b binding protein (cab) promoters" Plant Molecular Biology, 12(2):169-179 (Feb. 1989).
Murashige and Skoog, "A Revised Medium for Rapid Growth and Bio Assays with Tobacco Tissue Cultures", Physiologia Plantarum, 15:471-497 (1962).
Parra et al., "A combined action of pulmonary surfactant proteins SP-B and SP-C modulates permeability and dynamics of phospholipid membranes", Biochem J., 438:555-564 (2011).
Sambrook and Russell, "Molecular Cloning a Laboratory Manual", Third Edition, Cold Spring Harbor Laboratory Press, (2001) (21 pages).
Seehase et al., "New Surfactant with SP-B and C Analogs Gives Survival Benefit after Inactivation in Preterm Lambs", PLoS One 7(10): e47631 (Oct. 2012) (10 pages).
Stevens and Sinkin, Surfactant Replacement Therapy, Chest Topics in Practice Management, 131(5):1577-1582 (2007).
Tindamanyire et al., "Building a bi-directional promoter binary vector from the intergenic region of Arabidopsis thaliana cab 1 and cab2 divergent genes useful for plant transformation" African Journal of Biotechnology 12(11):1203-1208, (Mar. 13, 2013).
Wang et al., "A universal and rapid protocol for protein extraction from recalcitrant plant tissues for proteomic analysis", Electrophoresis, 27:2782-2786 (2006).
Weaver and Conkright, "Functions of Surfactant Proteins B and C", Annu. Rev. Physiol., 63:555-578 (2001).
Whitsett and Weaver, "Hydrophobic Surfactant Proteins in Lung Function and Disease", Mechanisms of Disease, N. Engl. J. Med., 347(26):2141-2148 (Dec 2002).
Wilson and Notter, "The Future of Exogenous Surfactant Therapy", Respiratory Care, 56(9):1369-1388 (Sep. 2011).
Yurdakok, M., "Inherited disorders of neonatal lung diseases", The Turkish Journal of Pediatrics, 46:105-114 (2004).
Zuo et al., "Current perspectives in pulmonary surfactant-Inhibition, enhancement and evaluation", Biochimica et Biophysica Acta, 1778:1947-1977 (2008).
International Preliminary Report on Patentability for: Int. App No. PCT/182014/061494, dated Dec. 29, 2015 (6 pages).
International Search Report for: Int. App No. PCT/182014/061494, dated Oct. 15, 2014 (4 pages).
Supplementary International Search Report for Int. App No. PCT/IB2015/052503, dated Mar. 11, 2016 (6 pages).

\* cited by examiner

SYNTHETIC PROMOTER CONSTRUCT FOR TRANSGENE EXPRESSION

CROSS-REFERENCE TO RELATED APPLICATIONS

This application claims the benefit of South African Provisional Patent Application No. 2014/03606, filed on May 19, 2014, the entire contents of which are hereby incorporated by reference.

TECHNICAL FIELD

This invention relates to regulation of gene expression in plants.

BACKGROUND

Unreliable and low-level constitutive transgene expression in plants is one of the major challenges in plant biotechnology applications for crop improvement and biopharming. Several molecular elements may play a role, but low-level expression of transgenes is primarily due to weak promoters. Currently, the choice of available promoters is limited and the majority of these promoters are based on conventional wild-type promoter elements of which the cauliflower mosaic virus 35S (CaMV 35S) is one of the most widely used promoters.

However, there is a need to drive transgene expression at levels higher than which is capable by the wild-type and even modified versions of CaMV 35S, especially for biopharming applications.

SUMMARY OF THE INVENTION

Disclosed herein are synthetic promoter constructs for enhanced transgene expression in plants; expression cassettes comprising the synthetic promoter constructs; and methods of expressing transgenic proteins in plants using the synthetic promoter constructs.

Provided herein is an isolated polynucleotide comprising a regulatory nucleic acid sequence that either (a) has at least 95% or more sequence identity to a polynucleotide sequence set forth in any one of SEQ ID NOs: 1, 3, 4 or 18, or a functionally equivalent fragment thereof, or (b) hybridises under stringent conditions to the complement of a polynucleotide sequence set forth in any one of SEQ ID NOs: 1, 3, 4 or 18.

In some embodiments, the regulatory nucleic acid sequence has 95%, 96%, 97%, 98%, 99%, or 100% sequence identity to any one of SEQ ID NOs: 1, 3, 4 or 18 or a functionally equivalent fragment thereof. In some embodiments, the the regulatory nucleic acid sequence has 100% sequence identity to any one of SEQ ID NOs: 1, 3, 4 or 18 or a functionally equivalent fragment thereof.

In some embodiments, the regulatory nucleic acid sequence or functionally equivalent fragment thereof contains one or more motifs selected from the group consisting of SORLREP2AT, ASF1MOTIFCAMV, AS1CAMV (SEQ ID NO:37), ATRICHPSPETE (SEQ ID NO:39), GT1MOTIFPSRBCS (SEQ ID NO:41), INRNTPSADB, CTRMCAMV35S, −10PEHVPSBD, LTREATLTI78, CBFHV, DRECRTCOREAT, LTRECOREATCOR15, MYCCONSENSUSAT, LRENPCABE, SORLIP1AT, BOXIIPCCHS, CCA1ATLHCB1, CGF1ATCAB2 (GATAAAGATTACTTCAGATATAACAAACGTTAC, SEQ ID NO: 45), GT1CONSENSUS, IBOXCORE, RBCSCONSENSUS, CIACADIANLELHC (SEQ ID NO:40), GATABOX, SORLIPSAT, and CACTFTPPCA1.

The isolated polynucleotide can further comprise one or more restriction enzyme sites for inserting a second nucleic acid sequence that is heterologous to the regulatory nucleic acid sequence, such that the inserted second nucleic acid sequence would be operably linked to the regulatory nucleic acid sequence, and the regulatory nucleic acid sequence is capable of directing transcription of the second operably linked nucleic acid sequence.

In some embodiments, the second nucleic acid sequence encodes a target protein heterologous to the regulatory nucleic acid sequence and is operably linked to the regulatory nucleic acid sequence. For example, the second nucleotide sequence can encode a target protein useful in the food or beverage industries, the pharmaceutical industry (e.g., as vaccines or therapeutic proteins), in agriculture, or in the chemical industry. In some embodiments, the second nucleotide sequence encodes a therapeutic protein. In some embodiments, the second nucleotide sequence encodes one or more copies of: (A) a pulmonary surfactant protein-B (SP-B) pre-proprotein or a functional fragment or analog thereof; (B) SP-B mature peptide or a functional fragment or analog thereof; or both (A) and (B).

In some embodiments, the isolated polynucleotides further comprise a terminator sequence, for example, a terminator sequence selected from a Nos poly A, a 35S poly A, a RbcS1 terminator or another terminator known to those skilled in the art. The regulatory nucleic acid sequence or functionally equivalent fragment thereof can be operably linked to the terminator sequence.

The isolated polynucleotides can further comprise one or more of the following elements:
(i) a polynucleotide sequence encoding a signal peptide such as the signal peptide region of equistatin or the signal peptide region of *Nicotiana tabacum* thionin (NtSP);
(ii) a polynucleotide sequence encoding a trafficking peptide such as an endoplasmic reticulum (ER)-trafficking peptide e.g., SEKDEL (SEQ ID NO:34), KDEL (SEQ ID NO:35), HDEL (SEQ ID NO:36); an oil body-trafficking peptide (e.g. oleosin), a protein storage vacuole-trafficking peptide (e.g., a Vacuolar Sorting Determinant (VSD) from for example, barley lectin, common bean phaseolin, or soybean β-conglycinin α' subunit); a plastid, including a chloroplast, chromoplast or leucoplast-trafficking peptide (e.g., a peptide capable of interacting with the thylakoid membrane of a plastid such as the chloroplast targeting signal from the small subunit of Rubisco from *Solanum*); or another trafficking peptide known to those skilled in the art;
(iii) a polynucleotide sequence encoding a tag such as polyhistidine, Leptin, late embryogenesis abundant protein (LEA), Lectin, maltose binding protein (MBP) or glutathione S-transferase (GST), or other tags known to those skilled in the art;
(iv) a polynucleotide sequence encoding a marker protein for detection, such as yellow fluorescent protein (YPet), green fluorescent protein (GFP), chloramphenicol acetyl transferase (CAT), luciferase, or others known to those skilled in the art;
(v) a polynucleotide sequence encoding a protease cleavage site, such as any one or more of an enterokinase, chymosin or Tobacco Etch Virus (TEV) protease cleavage site; or
(vi) a psbA regulatory 5'-UTR or 3' UTR region for targeting a plastid, such as a chloroplast.

Also provided is an expression cassette for expressing proteins in a plant cell or a plant. The expression cassette comprises the isolated polynucleotides described herein. The plant-based expression cassettes may be suitable for *Agrobacterium tumefaciens*-mediated transformation.

Also provided is a plant cell comprising any of the isolated polynucleotides or plant-based expression cassettes described herein. The plant cell may be in a plurality of plant cells in suspension culture, in plant cells in tissue culture, in plant cells in a leaf of a plant or a transgenic plant or any part thereof. The plant cell may be from a monocot or dicot plant. In some embodiments, the plant is a *Nicotiana tobacum* plant.

Also provided are plant progenies or seeds comprising any of the isolated polynucleotides or plant-based expression cassettes described herein.

Also provided herein is a method of expressing a target protein in a plant by introducing the isolated polynucleotides described herein into a plant cell, and expressing the target protein in the plant cell. The method can further include a step of exposing the plant cell to one or more induction stimuli. For example, such induction stimuli may be any one or more of different intensities and periods of light exposure, cold shock, heat shock, induction of drought conditions or hormone induction such as by Abscisic Acid (ABA).

An "isolated" polynucleotide means a polynucleotide that is synthesized or separated from its native environment and present in sufficient quantity to permit its identification or use. An isolated polynucleotide can be one that is (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated polynucleotide is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleotide sequence existing in its native state in its natural host is not. An isolated polynucleotide can be substantially purified, but need not be. In the context of the present invention, polynucleotide, is used interchangeably with the term "nucleic acid."

As used herein, a "regulatory nucleic acid sequence" refers to a sequence of DNA that is usually, but not always, located upstream (5') to a coding sequence, and controls the expression of the coding sequence by providing the recognition for RNA polymerase and/or other factors required for transcription to start at a particular site. An example of a regulatory nucleic acid sequence is a promoter. A promoter comprises a core promoter element, responsible for the initiation of transcription, as well as other regulatory elements that modify gene expression. It is to be understood that nucleotide sequences, located within introns, or 3' of the coding sequence may also contribute to the regulation of expression of a coding sequence.

The term "functionally equivalent fragment" used herein refers to a portion of the regulatory nucleic acid sequence that retains at least 20% (e.g., at least: 30%; 40%; 50%; 60%; 70%; 75%; 80%; 85%; 90%; 95%; 97%; 98%; 99%; or all) of the biological activity of the regulatory nucleic acid sequence in regulating the expression of an operably linked coding sequence. Methods of measuring and comparing the relative regulatory activity of nucleic acid sequences are well known in the art.

As used herein, the term "sequence identity" refers to the degree of identity between any given query sequence and a subject sequence. Percentage of "sequence identity" is determined by comparing two optimally aligned sequences over a comparison window, where the fragment of the nucleotide sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity. The output is the percent identity of the subject sequence with respect to the query sequence. Various means for determination of percent sequence identity between two particular polynucleotide sequences are well known to those skilled in the art. For example, one method for use is the Basic Local Alignment Search Tool (BLAST) tool that finds regions of local similarity between sequences (www.ncbi.nlm.nih.gov/blast/).

The term "operably linked" used herein means the transcription or translation of a heterologous nucleotide sequence is under the influence of the regulatory nucleic acid sequence. "Operably linked" is also intended to mean the joining of two nucleotide sequences such that the coding sequence of each DNA fragment remain in the proper reading frame.

A "heterologous" polynucleotide sequence or protein is a sequence or protein that is not naturally operably linked to and regulated by the regulatory nucleic acid sequence.

The term "analog" is used herein to refer to a protein or peptide molecule that structurally and/or functionally resembles a reference protein or peptide molecule, but contains at least one modification, addition, deletion, or substitution of one or more amino acid residues.

"Stringent conditions" or "stringent hybridization conditions" used herein refers to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Typically, stringent conditions will be those in which the salt concentration is about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
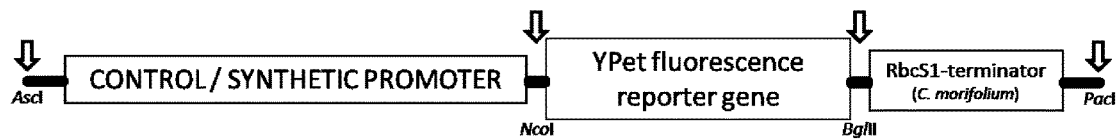
FIG. 1 shows a representative graphical illustration of the promoter expression cassette described herein.

Provided herein are synthetic promoter constructs for enhanced transgene expression in plants; expression cassettes comprising the synthetic promoter constructs; and methods of expressing transgenic proteins in plants using the synthetic promoter constructs.

Temporal and/or spatial control of transgene expression in plants is desirable in many agricultural and biopharmaceutical applications. One way of achieving such control is by rational design of the regulatory nucleic acid sequence, for example, the promoter. Promoters can be inducible, constitutive and/or tissue-specific. Promoter engineering applications for targeted control of transgene activity in plants include biotic and abiotic stress tolerance, high-level transgene expression and sensing environmental and/or chemical stimuli. Depending on the biotechnological application, e.g., crop improvement or commercially viable expression of a biopharmaceutical peptide, both high-level constitutive and targeted/inducible transgene expression systems are important.

Strong constitutive transgene expression continues to be a desirable trait. The Cauliflower Mosaic Virus 35S (CaMV 35S) promoter [Benfey and Chua 1990], and recombinant modifications thereof, e.g. native CaMV 35S plus an additional 35S subdomain-B acting as an enhancer, have been used extensively for high level transgene expression in plants [Benfey et al 1990; Bhullar et al. 2003, 2007]. However, currently, the choice and availability of strong constitutive promoters with comparable or even better activity than CaMV 35S is still relatively limited.

The challenges in plant genetic engineering studies, e.g., promoter availability, insufficient levels of transgene expression, and homology-dependent gene silencing (HDGS), necessitate the engineering and use of novel synthetic promoters [Venter and Botha 2010]. In addition to the design of novel synthetic strong constitutive promoters, specific cis-motif architecture within regulatory promoter modules, may allow for predictive applications to confer inducible expression in response to various environmental, physical or chemical stimuli [Venter 2007]. Compared to conventional wild-type promoters from viral and/or plant origin, well-designed synthetic promoters may offer superior transgene expression levels, refine control of transgene (or multiple transgene) expression and limit homology-dependent gene silencing in plant genetic engineering applications.

The applicant has therefore developed 21 candidate synthetic promoters for testing in transgenic plant lines using a stepwise approach by: 1) identifying promoters of genes known to be highly expressed in plants (for example, by literature searches), 2) selecting specific regions in those promoters (regulatory modules) based on the presence of specific plant transcription factor (TF) binding sites (or cis-motifs), for example by using a database of known motifs such as PLACE (Higo et al., 1999) or PlantCARE (Lescot et al., 2002), 3) combining different and/or repeated promoter modules to construct synthetic promoters and 4) in vivo testing of the candidate synthetic promoter constructs in transgenic plant lines for efficient expression of a transgenic protein.

Examples of regulatory modules selected for synthetic promoter design included:
  Promoters known for high-level transgene expression in plants;
  Genes known to be expressed at high levels in plants;
  Promoters associated with photosynthesis; and
  Plant transcription factor binding sites as detected with PLACE [Higo et al., 1999].

Furthermore, cis-motif selections with the use of PLACE [Higo et al., 1999] were primarily based on:
  Light regulation, activation;
  Leaf specific expression;
  Motifs known to act as enhancers;
  Motifs associated with low temperature responsiveness; and
  Motifs from specific promoters, e.g., CaMV 35S and Ribulose-1,5-bisphosphate carboxylase small subunit promoter (RBCss) known to drive high-level transgene expression in plants.

The candidate regulatory modules were designed and/or extended to comprise a majority selection of the above-mentioned cis-motifs, which include motifs that function as inducible elements. Accordingly, a person skilled in the art would appreciate that the method may comprise a step of exposing the plant cell to one or more induction stimuli, including different intensities and periods of light exposure, cold shock, heat shock, induction of drought conditions or hormone induction such as by Abscisic Acid (ABA).

The 21 candidate synthetic promoters were then tested in transgenic tobacco plants with the use of a fluorescent reporter protein, YPet (Yellow Fluorescent Protein), although any other reporter protein known to those skilled in the art may be used, such as luciferase, green fluorescent protein (GFP), chloramphenicol acetyl transferase (CAT) and the like. Interestingly, most of the candidate synthetic promoters designed based using an in silico rational design strategy did not show marked improvement, or performed worse than the control CaMV 35S promoters. This demonstrates the necessity for performance of in vivo testing in order to determine the efficacy of a synthetic promoter construct. Evidence of efficacy in silico is not sufficient. However, several first generation transgenic plant lines from various synthetic promoter constructs did show enhanced YPet expression compared to the control CaMV 35S promoters and one of the synthetic promoter constructs in particular showed exceptionally improved protein expression: it increased protein expression about 5 times more than the highest performing control 2×CaMV 35S promoter.

Accordingly, provided herein are isolated polynucleotides comprising a regulatory nucleic acid sequence. The regulatory nucleic acid sequence can be or contain, a sequence having at least 80% sequence identity (e.g., at least 85%, 90%, 95%, 96%, 97%, 98%, 99%, or 100% sequence identity) to any one of the polynucleotide sequences set forth in SEQ ID NOs: 1, 3, 4, or 18, or a functionally equivalent fragment thereof. In some embodiments, the regulatory nucleic acid sequence has 95%, 96%, 97%, 98%, 99%, or 100% sequence identity to any one of SEQ ID NOs: 1, 3, 4 or 18 or a functionally equivalent fragment thereof. In some embodiments, the the regulatory nucleic acid sequence has 100% sequence identity to any one of SEQ ID NOs: 1, 3, 4 or 18 or a functionally equivalent fragment thereof.

The regulatory nucleic acid sequence can also be or contain, a sequence that hybridises under stringent conditions to the complement of any one of SEQ ID NOs: 1, 3, 4 or 18. Hybridization conditions are well known to those skilled in the art. "Stringent conditions" or "stringent hybridization conditions" used herein refers to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, often less than 500 nucleotides in length.

Typically, stringent conditions will be those in which the salt concentration is about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary stringent conditions include hybridization in 6× sodium chloride/sodium citrate (SSC) at 37° C., followed by a wash in 0.5× or 1×SSC at 55 to 60° C. Exemplary high stringency conditions include hybridization in 6×SSC at 45° C., followed by a wash in 0.2×SSC, 0.1% SDS at 65° C. Duration of hybridization is generally less than about 24 hours, usually about 4 to about 12 hours.

In some embodiments, the regulatory nucleic acid sequence or functionally equivalent fragment thereof may contain one or more motifs selected from the group consisting of SORLREP2AT, ASF1MOTIFCAMV, AS1CAMV (SEQ ID NO:37), ATRICHPSPETE (SEQ ID NO:39), GT1MOTIFPSRBCS (SEQ ID NO:41), INRNTPSADB, CTRMCAMV35S, -10PEHVPSBD, LTREATLTI78, CBFHV, DRECRTCOREAT, LTRECOREATCOR15, MYCCONSENSUSAT, LRENPCABE, SORLIP1AT, BOXIIPCCHS, CCA1ATLHCB1, CGF1ATCAB2 (SEQ ID NO: 45), GT1CONSENSUS, IBOXCORE, RBCSCONSENSUS, CIACADIANLELHC (SEQ ID NO:40), GATABOX, SORLIP5AT, and CACTFTPPCA1. It is noted that the motifs provided above are annotated as set out in the PLACE database (Higo et al., 1999), but may have a different annotation if using another database, such as Plant-CARE (Lescot et al., 2002). It is also noted that the motifs shown by the sequences depicted in Table 1 can be in the 5'-3' orientation (+) or the reverse 3'-5' orientation (−).

The isolated polynucleotides can further comprise one or more restriction enzyme sites for inserting a second nucleic acid sequence that is heterologous to the regulatory nucleic acid sequence, such that the inserted second nucleic acid sequence would be operably linked to the regulatory nucleic acid sequence, and the regulatory nucleic acid sequence is capable of directing transcription of the second operably linked nucleic acid sequence. In some embodiments, the second nucleic acid sequence encodes a target protein heterologous to the regulatory nucleic acid sequence and is operably linked to the regulatory nucleic acid sequence.

The promoters described herein can be used as strong constitutive promoters for high-level transgene expression in the food and beverage industries, the pharmaceutical industry (e.g., as vaccines or therapeutic proteins), the agriculture industry, or the chemical industry amongst others. It is recognized that any gene of interest can be operably linked to the promoter sequences disclosed herein and expressed in plants.

In one embodiment of the invention, the expressed transgenic protein is a protein useful in the pharmaceutical industry, in particular, a therapeutic protein. A particular embodiment of the invention, the expressed transgenic protein is a pulmonary surfactant protein-B (SP-B) pre-proprotein, or SP-B mature peptide, functional fragment, or analog thereof [Pryhuber 1998].

Accordingly, the second nucleotide sequence can encode a target protein useful in the food or beverage industries, the pharmaceutical industry, in agriculture, or in the chemical industry. In some embodiments, the second nucleotide sequence encodes a therapeutic protein. In some embodiments, the second nucleotide sequence encodes one or more copies of: (A) a pulmonary surfactant protein-B (SP-B) pre-proprotein or a functional fragment or analog thereof; (B) SP-B mature peptide or a functional fragment or analog thereof; or both (A) and (B).

Apart from the target transgenic protein, the regulatory nucleic acid sequence or functionally equivalent fragment thereof can be operably linked to one or more elements known to those skilled in the art, including, but not limited to the following:
  (i) a polynucleotide sequence encoding a signal peptide such as the signal peptide region of equistatin or the signal peptide of Nicotiana tabacum thionin (NtSP);
  (ii) a polynucleotide sequence encoding a trafficking peptide such as an endoplasmic reticulum (ER)-trafficking peptide e.g., SEKDEL (SEQ ID NO:34), KDEL (SEQ ID NO:35), HDEL (SEQ ID NO:36); an oil body-trafficking peptide (e.g. oleosin), a protein storage vacuole-trafficking peptide (e.g., a Vacuolar Sorting Determinant (VSD) from for example, barley lectin, common bean phaseolin, or soybean β-conglycinin α' subunit); a plastid, including a chloroplast, chromoplast or leucoplast-trafficking peptide (e.g., a peptide capable of interacting with the thylakoid membrane of a plastid such as the chloroplast targeting signal from the small subunit of Rubisco from Solanum); or another trafficking peptide known to those skilled in the art;
  (iii) a polynucleotide sequence encoding a tag such as polyhistidine, Leptin, late embryogenesis abundant protein (LEA), Lectin, maltose binding protein (MBP) or glutathione S-transferase (GST), or other tags known to those skilled in the art for improved protein expression, stability or purification;

(iv) a polynucleotide sequence encoding a marker protein for detection, such as yellow fluorescent protein (YPet), green fluorescent protein (GFP), chloramphenicol acetyl transferase (CAT), luciferase, or others known to those skilled in the art; and (v) a polynucleotide sequence encoding a protease cleavage site flanking the target protein, such as any one or more of an enterokinase, chymosin or Tobacco Etch Virus (TEV) protease cleavage site, for release of the target protein of interest by proteolytic cleavage.

Furthermore, the regulatory nucleic acid sequence or functionally equivalent fragment thereof of the invention can be operably linked to a psbA regulatory 5'-UTR and 3' UTR region for targeting a plastid, in particular a chloroplast.

In some embodiments, the isolated polynucleotides further comprise a terminator sequence, for example, a terminator sequence selected from a Nos poly A, a 35S poly A, a RbcS1 terminator or another terminator known to those skilled in the art. The regulatory nucleic acid sequence or functionally equivalent fragment thereof may be operably linked to the terminator sequence.

Also provided herein are expression cassettes comprising the isolated polynucleotides described herein. The expression cassettes can be suitable for *Agrobacterium tumefaciens*-mediated transformation. The expression cassette can include a regulatory nucleic acid sequence that either (a) has at least 95% or more sequence identity to a polynucleotide sequence set forth in any one of SEQ ID NOs: 1, 3, 4 or 18, or a functionally equivalent fragment thereof, or (b) hybridises under stringent conditions to the complement of a polynucleotide sequence set forth in any one of SEQ ID NOs: 1, 3, 4 or 18. The expression cassette can further include a second nucleic acid sequence that is operably linked to the regulatory nucleic acid sequence and the regulatory nucleic acid sequence is capable of directing transcription of the second operably linked nucleic acid sequence. The second nucleic acid sequence can encode a target protein useful in the food or beverage industries, the pharmaceutical industry (e.g., as vaccines or therapeutic proteins), in agriculture, or in the chemical industry. In some embodiments, the second nucleotide sequence encodes a therapeutic protein, for example, a pulmonary surfactant protein-B (SP-B) pre-proprotein, or SP-B mature peptide, functional fragment, or analog thereof.

The expression cassette can further comprise one or more of the following elements:

(i) a polynucleotide sequence encoding a signal peptide such as the signal peptide region of equistatin or the signal peptide region of *Nicotiana tabacum* thionin (NtSP);

(ii) a polynucleotide sequence encoding a trafficking peptide such as an endoplasmic reticulum (ER)-trafficking peptide e.g., SEKDEL (SEQ ID NO:34), KDEL (SEQ ID NO:35), HDEL (SEQ ID NO:36); an oil body-trafficking peptide (e.g. oleosin), a protein storage vacuole-trafficking peptide (e.g., a Vacuolar Sorting Determinant (VSD) from for example, barley lectin, common bean phaseolin, or soybean β-conglycinin α' subunit); a plastid, including a chloroplast, chromoplast or leucoplast-trafficking peptide (e.g., a peptide capable of interacting with the thylakoid membrane of a plastid such as the chloroplast targeting signal from the small subunit of Rubisco from *Solanum*); or another trafficking peptide known to those skilled in the art;

(iii) a polynucleotide sequence encoding a tag such as polyhistidine, Leptin, late embryogenesis abundant protein (LEA), Lectin, maltose binding protein (MBP) or glutathione S-transferase (GST), or other tags known to those skilled in the art;

(iv) a polynucleotide sequence encoding a marker protein for detection, such as yellow fluorescent protein (YPet), green fluorescent protein (GFP), chloramphenicol acetyl transferase (CAT), luciferase, or others known to those skilled in the art;

(v) a polynucleotide sequence encoding a protease cleavage site, such as any one or more of an enterokinase, chymosin or Tobacco Etch Virus (TEV) protease cleavage site; or (vi) a psbA regulatory 5'-UTR or 3' UTR region for targeting a plastid, such as a chloroplast.

Also provided are plant cells comprising any of the isolated polynucleotides or plant-based expression cassettes described herein. The plant cell may be a plurality of plant cells in suspension culture, plant cells in tissue culture, or plant cells in a leaf of a plant, a transgenic plant, or any part thereof. The plant cell may be from a monocot or dicot plant. In some embodiments, the plant is a *Nicotiana tobacum* plant. Also provided are plant progenies or seeds comprising any of the isolated polynucleotides or plant-based expression cassettes described herein.

Also provided herein are methods of expressing a target protein in a plant by introducing the isolated polynucleotides described herein into a plant cell, and expressing the target protein in the plant cell. The methods can further include a step of exposing the plant cell to one or more induction stimuli. For example, such induction stimuli may be any one or more of different intensities and periods of light exposure, cold shock, heat shock, induction of drought conditions or hormone induction such as by Abscisic Acid (ABA).

The invention will be described by way of the following examples which are not to be construed as limiting in any way the scope of the invention.

EXAMPLES

Example 1

1.1. Materials and Methods 1.1.1. Promoter Synthesis and Cloning in Plant Transformation Vector Synthesis and sub-cloning of all promoter expression cassettes were conducted by DNA2.0 (www.dna20.com) and Blue Heron Biotech (www.blueheronbio.com). Within ImpactVector 1.1 (Plant Research International, Wageningen; www.pri.wur.nl/UK/products/ImpactVector/) each promoter was synthesized between AscI/NcoI sites, replacing the RbcS1 promoter of *Chrysanthemum morifolium*. Each promoter expression cassette within ImpactVector 1.1 comprised of a promoter (synthetic or unmodified) driving a gene coding for YPet fluorescent protein, synthesized between NcoI/BglII sites, and a terminator of RbcS1 gene from *C. morifolium* between BglII/PacI sites (as illustrated in FIG. 1). Subsequently, each promoter expression cassette was excised and sub-cloned in a modified (to accommodate AscI and PacI restriction sites) binary vector suitable for *Agrobacterium*-mediated plant transformation.

1.1.2. Synthetic Promoter Design

Regulatory modules for synthetic promoter designs were based on various factors including:

Promoters known for high-level transgene expression in plants;
Genes known to be expressed at high levels in plants;
Promoters associated with photosynthesis; and Plant transcription factor binding sites as detected with PLACE [Higo et al., 1999].

In addition, cis-motif selections with the use of PLACE [Higo et al., 1999] were primarily based on:
Light regulation, activation;
Leaf specific expression;
Motifs known to act as enhancers;
Motifs associated with low temperature responsiveness; and
Motifs from specific promoters i.e. CaMV 35S and Ribulose-1,5-bisphosphate carboxylase small subunit promoter (RBCss) known to drive high-level transgene expression in plants.

The candidate regulatory modules were designed and/or extended to comprise a majority selection of the above-mentioned type cis-motifs, which include motifs that function as inducible elements.

Two promoters were chosen as control promoters for comparative analysis to 21 newly designed synthetic promoters. The control promoters were wild-type CaMV 35S promoter (Genbank Acc no. V00140) designated as C1 [SEQ ID NO:22] and a double enhancer CaMV 35S domain-B, also called 2×35S, that has an extension of 73 bp at Domain_B (Genbank AC: V00140.1) of the original 35S promoter, together with an additional Domain_B (with 73 bp extension) fused to it, and a 5'-UTR designated as C2 [SEQ ID NO:23]. The synthetic promoters were designated as AZprom-1 to AZprom-21.

Using the ImpactVector expression cassette and combining a binary vector such as pCAMBIA, specific restriction enzyme sites that should not cut in the promoters for sub-cloning purposes were identified. Where specific restriction enzyme sites were detected, revisions were proposed and sequences submitted to the PLACE database to revise the sequence in such a way that original putative transcription factor-binding sites remained identical to original sequence comprising restriction enzyme-site.

Table 1 shows the various cis-motifs present in the promoters selected to drive high-level expression of transgenes in plants. Table 2 shows the various candidate synthetic promoters designed for testing, including their size and components.

1.1.3. Generation of transgenic plants and genomic PCR

Tobacco plants (*Nicotiana tabacum* var Samsun) were maintained on MS medium in a temperature (22° C.) regulated growth room at a 16 hour light/8 hour dark photoperiod. Promoter expression cassettes sub-cloned in a binary vector were mobilized into *Agrobacterium tumefaciens* strain LBA4404 via electroporation and tobacco leaves were transformed using a standard leaf disc method [Horsch et al 1985]. Plantlets were regenerated under antibiotic selection on MS medium and primary transgenic tobacco plantlets were hardened off and grown in a containment glasshouse at 22° C. After approximately 12 weeks, plants were transferred to a growth room regulated at 24° C. with a 16 hour light/8 hour dark photoperiod at a light intensity of 316 μmol·m-2.s-1. To confirm transgenic status, genomic DNA was extracted from putative transgenic tobacco leaf material using the GeneJET Genomic DNA Purification Kit (Thermo Fisher Scientific Inc, USA). PCR was performed, using primers: YPet_frw (5'-CTCAGTAAGTGGGGAAGGT-GAAGGC-3') [SEQ ID NO: 27] and YPet_rev (5'-TGCCA-GCTGAACACCTCCATCCTCG-3') [SEQ ID NO: 28], at a predenaturation cycle of 94° C. for 2 min followed by 35 cycles of amplification (94° C. denaturation, 30 sec; 55° C. annealing, 30 sec; 72° C. polymerization, 30 sec) to amplify a 457 bp fragment using GoTaq® DNA Polymerase (Promega Corporation, Madison, USA). All PCR reactions were carried out in a Perkin-Elmer GeneAmp® Thermocycler 9700 (Perkin Elmer Corporation, Wellesley, USA) and PCR products were visualized in ethidium bromide-stained 1% (w/v) agarose gels.

TABLE 1

PLACE cis-motif analysis for synthetic promoter design

| MOTIF | Associated Function | CORE sequence | Description |
|---|---|---|---|
| -10PEHVPSBD | Circadian/Light | TATTCT | light regulation |
| AS1CAMV | Leaf | CCACTGACGTAAGGGATGACGCACAATCC (SEQ ID NO: 37) | (activation sequence 1) in CaMV 35 S |
| ASF1MOTIFCAMV | Light/Leaf | TGACG | ASF-1 binding site in CaMV 35 S |
| AT1BOX | Light/Leaf | AATATTTTATT (SEQ ID NO: 38) | AT-rich element |
| ATRICHPSPETE | Enhancer | AATATACTAGTATTATTTACTAAAAAAAATC (SEQ ID NO: 39) | AT-rich |
| BOXIIPCCHS | Light | ACGTGGC | BoxII |
| CACGTGMOTIF | Light/Leaf | CACGTG | G-Box |
| CACTFTPPCA1 | Leaf | (T/C)ACT | mesophyll-specific (CACT) |
| CCA1ATLHCB1 | Leaf | AA(C/A)AATCT | Phytochrome |
| CBFHV | Low Temp/Drought | (A/G)(C/T)CCGAC | CRT/DRE |
| CIACADIANLELHC | Circadian/Light/Leaf | CAANNNNATC (SEQ ID NO: 40) | Region identified for circadian expression |
| CTRMCAMV35S | Enhancer | TCTCTCTCT | CT-rich motif in CaMV 35 S |
| DRECRTCOREAT | Low Temp/Drought | (A/G)CCGAC | CRT/DRE |

TABLE 1-continued

PLACE cis-motif analysis for synthetic promoter design

| MOTIF | Associated Function | CORE sequence | Description |
|---|---|---|---|
| GATABOX | Leaf/Light | GATA | GATA motif in CaMV 35 S |
| GBOXLERBCS | Leaf/Light | (A/C)CACGTGGC | rbcS/G-box |
| GT1MOTIFPSRBCS | Light/Leaf | (G/T)(A/T)GTG(A/G)(A/T)AA(A/T)(A/G)(A/T) (SEQ ID NO: 41) | RBCS/BoxII/GT-1 |
| GT1CONSENSUS | Light/Leaf | G(A/G)(A/T)AA(A/T) | GT-1 |
| HY5AT | Light | TGACACGTGGCA (SEQ ID NO: 42) | G-box |
| IBOX | Light/Leaf | GATAAG | I-box/rbcS |
| IBOXCORE | Light/Leaf | GATAA | I-box |
| INRNTPSADB | Light | (C/T)TCANT(C/T)(C/T) | 'Initiator-element'/ TATA-less promoter |
| LBOXLERBCS | Light/Leaf | AAATTAACCAA (SEQ ID NO: 43) | rbcS |
| LREBOXIPCCHS1 | Light/Leaf | AACCTAACCT (SEQ ID NO: 44) | BoxI |
| LRENPCABE | Light/Leaf | ACGTGGCA | LRE-element |
| LTREATLTI78 | Low Temp/Leaf | ACCGACA | LTRE |
| LTRE1HVBLT49 | Low Temp/Leaf | CCGAAA | LTRE |
| LTRECOREATCOR15 | Low Temp/Leaf | CCGAC | LTRE |
| MYCCONSENSUSAT | Drought/Low Temp/Leaf | CANNTG | Leaf/ICE-1 |
| RBCSCONSENSUS | Leaf | AATCCAA | rbcS/G-box/I-box |
| SORLIP1AT | Light | GCCAC | Phytochrome-reg |
| SORLIP5AT | Light | GAGTGAG | Phytochrome-reg |
| SORLREP2AT | Light | ATAAAACGT | Phytochrome-reg |
| SORLREP3AT | Light | TGTATATAT | Phytochrome-reg |
| SV40COREENHAN | Enhancer | GTGG(A/T)(A/T)(A/C/T)G | SV40 core enhancer |

TABLE 2

Candidate synthetic promoters

| Name | Size (bp)* | Description of Components |
|---|---|---|
| AZprom_1 [SEQ ID NO: 1] | 951 | Pea plastocyanin promoter region (−784 to −176) (Genbank: X68313) Vacuolar Pyrophosphatase VPP (Grapevine) core promoter for PIC assembly (342 bp upstream from VPPase ATG-start codon) |
| AZprom_2 [SEQ ID NO: 2] | 1149 | 3x copies of the wheat cab-1 enhancer (−357 to −89) (Genbank: X05823) plus 3' cytosine residue Vacuolar Pyrophosphatase VPP (Grapevine) core promoter for PIC assembly plus native grapevine VPP 5'-UTR region |
| AZprom_3 [SEQ ID NO: 3] | 1039 | 2x copies of pea plastocyanin enhancer (original 268 bp extended to 445 bp) (Genbank: X68313) CaMV 35S minimal promoter (−90 to +8) pea plastocyanin 5'-UTR (52 bp, as calculated from pea plastocyanin TSS at −53 bp) |
| AZprom_4 [SEQ ID NO: 4] | 1232 | 2x copies of pea plastocyanin enhancer (original 268 bp extended to 445 bp) (Genbank: X68313) Vacuolar Pyrophosphatase VPP (Grapevine) core promoter for PIC assembly plus native grapevine VPP 5'-UTR region |

TABLE 2-continued

Candidate synthetic promoters

| Name | Size (bp)* | Description of Components |
|---|---|---|
| AZprom_5 [SEQ ID NO: 5] | 1149 | 3x copies of the wheat cab-1 enhancer (−357 to −89) (Genbank: X05823) plus 3' cytosine residue in reverse orientation to AZprom_2<br>Vacuolar Pyrophosphatase VPP (Grapevine) core promoter for PIC assembly plus native grapevine VPP 5'-UTR region |
| AZprom_6 [SEQ ID NO: 6] | 867 | 4x copies of the spinach plastocyanin enhancer (−259 to −79) (Genbank: X52288)<br>Core/minimal-promoter of spinach plastocyanin PLUS native 5'-UTR region |
| AZprom_7 [SEQ ID NO: 7] | 1066 | 4x copies of the spinach plastocyanin enhancer (−259 to −79) (Genbank: X52288)<br>Vacuolar Pyrophosphatase VPP (Grapevine) core promoter for PIC assembly plus native grapevine VPP 5'-UTR region |
| AZprom_8 [SEQ ID NO: 8] | 1405 | 1x copy of CaMV 35S Domain B (−343 to −91) enhancer<br>*Arabidopsis* Plastocyanin promoter region (includes 5'-UTR region) (NC_003070.9_Ath Plastocyanin_NCBI) |
| AZprom_9 [SEQ ID NO: 9] | 1424 | VPP (M10.A) promoter region plus ASF1MOTIFCAMV, CTRMCAMV35S and VPP promoter region: −1430 to −159 relative to start codon<br>CaMV 35S minimal promoter (Domain A: −90 +8)<br>Chrysanth rbcS 5'-UTR (AY163904) |
| AZprom_10 [SEQ ID NO: 10] | 1004 | 2x copies of the spinach plastocyanin enhancer (−259 to −79) (Genbank: X52288)<br>VPP (M10.A) promoter region plus CBFHV, DRECRTCOREAT, LTREATLTI78, LTRE1HVBLT49, LTRECOREATCOR15, MYCCONSENSUSAT, ASF1MOTIFCAMV, CTRMCAMV35S and VPP promoter region: −642 to start codon |
| AZprom_11 [SEQ ID NO: 11] | 895 | 1x copy of CaMV 35S Domain B (−343 to −91) enhancer<br>VPP (M10.A) promoter region plus CBFHV, DRECRTCOREAT, LTREATLTI78, LTRE1HVBLT49, LTRECOREATCOR15, MYCCONSENSUSAT, ASF1MOTIFCAMV, CTRMCAMV35S and VPP promoter region: −642 to start codon |
| AZprom_12 [SEQ ID NO: 12] | 1415 | VPP (M10.A) promoter region plus ASF1MOTIFCAMV, CTRMCAMV35S and VPP promoter region: −1430 to −159 relative to start codon<br>Core/minimal-promoter of spinach plastocyanin PLUS native 5'-UTR region |
| AZprom_13 [SEQ ID NO: 13] | 848 | 2x CaMV 35S Domain B (−343 to −91) enhancer<br>Vacuolar Pyrophosphatase VPP (Grapevine) core promoter for PIC assembly plus native grapevine VPP 5'-UTR region |
| AZprom_14 [SEQ ID NO: 14] | 1148 | 2x CaMV 35S Domain B (−343 to −91) enhancer<br>VPP (M10.A) promoter region plus CBFHV, DRECRTCOREAT, LTREATLTI78, LTRE1HVBLT49, LTRECOREATCOR15, MYCCONSENSUSAT, ASF1MOTIFCAMV, CTRMCAMV35S and VPP promoter region: −642 to start codon |
| AZprom_15 [SEQ ID NO: 15] | 1049 | 1x CaMV 35S Domain B (−343 to −91) enhancer<br>*Arabidopsis* photosystem I subunit O (PSO-1) promoter region (Genbank: NM_100711) |
| AZprom_16 [SEQ ID NO: 16] | 977 | 1x copy of the spinach plastocyanin enhancer (−259 to −79) (Genbank: X52288)<br>*Arabidopsis* photosystem I subunit O (PSO-1) promoter region (Genbank: NM_100711) |
| AZprom_17 [SEQ ID NO: 17] | 743 | 1x CaMV 35S Domain B (−343 to −91) enhancer<br>2x copies of the Ath PSBP-1 selected region (Genbank no. X98108) (−241 to −76 relative to start codon)<br>CaMV 35S Domain A minimal promoter (−90 to +8)<br>5'-UTR region of tobacco rbc_ss region (−61 bp relative to start codon) (Tobacco_rbcss_EPD: X02353) |
| AZprom_18 [SEQ ID NO: 18] | 794 | 2x copies of the Ath cab2 selected region (−115 relative to TATA-box) (Genbank: X15221)<br>Ath cab2 promoter region (−564 relative to start codon) |

TABLE 2-continued

Candidate synthetic promoters

| Name | Size (bp)* | Description of Components |
|---|---|---|
| AZprom_19 [SEQ ID NO: 19] | 863 | 2x copies of VPP_mod promoter [SEQ ID NO: 24]<br>1x Tobacco core promoter + 5'-UTR (−131 bp relative to start codon) (Tobacco_rbcss_EPD: X02353) |
| AZprom_20 [SEQ ID NO: 20] | 934 | 2x copies of RBCss_mod promoter [SEQ ID NO: 25] (Tobacco_rbcss_EPD: X02353)<br>VPP core promoter + 5'-UTR (−131 bp relative to start codon) |
| AZprom_21 [SEQ ID NO: 21] | 1400 | 1x copy of CaMV 35S Domain B (−343 to −91) enhancer<br>1x inverted DR region of Ft-PEPc promoter [SEQ ID NO: 26]<br>Proximal region (PR) of Ft-PEPc promoter |

*without YPet ATG

1.1.4. Fluorescence Screening

The YPet reporter is a yellow fluorescent protein (YFP) modified for Forster resonance energy transfer (FRET) applications with an excitation at 517 nm and emission at 530 nm. Rapid visual screening was conducted using a handheld ROFIN Polilight FLARE PLUS 2 forensic flashlight (ROFIN forensics, Australia) with a Cyan LED output of 485 nm to 515 nm and orange filter goggles with a range of 190 nm to 545 nm. Plants transferred to the growth room were continuously screened for 8 to 12 weeks. Highest YPet fluorescence from 35S and 2×35S leaves was used as comparison to screen synthetic promoter plant lines. Plant lines, ranging from 20 cm to 40 cm in height, of which the top 3 leaves had a lower YPet fluorescence were discarded. Plants not discarded were analyzed using a nanodrop fluorospectrometer (Thermo Fisher Scientific Inc, USA).

1.1.5. Sampling

Selected tobacco plants were at least 30 cm high (from top of soil in pot). A 10 mm diameter cork-bore tool was used to punch 10 mm leaf-discs out of tobacco leaves. Each 10 mm leaf-disc was punched near the middle of leaf next to, but not including the middle vein, but including a side vein. Five different leaves, designated as L1, L2, L3, L4 and L5 were sampled. The first leaf (L1) was the first leaf of at least 10 cm in length. The following leaves going down the plant were then sampled up until the fifth leaf. Each fifth leaf had 5 leaf-discs punched out of the middle of the leaf for analysis.

1.1.6. YPet Protein Extraction

Extraction buffer used was 1×PBS (Sigma 79383) with 2% 2-mercaptoethanol. Five 10 mm leaf-discs (per leaf) per extract were added to 1 mL of extraction buffer in 2 ml eppendorf tubes. Two 4 mm stainless steel balls were placed in each eppendorf tube. The tubes were placed in a tissue-lyzer and shaken at 15 min/30 rpm. Next, 500 µl of chloroform was added. The tubes were then vortexed vigorously for 20 seconds and centrifuged for 10 min at maximum speed (13000 rpm). Supernatent was removed (300 mL to 500 mL) and used to measure fluorescence intensity.

1.1.7. Fluorescence Intensity Measurement

The Nanodrop ND3300 protocol for YPet detection (White LED) was used with extraction buffer (1×PBS) as the blank reading. The wild-type plant reading was performed and the blank reading was deducted as background fluorescence. 2 µl of extracts were analysed and the reading was obtained as relative fluorescent unit (RFU) values.

1.1.8. Total Protein Quantification

Proteins were extracted using the Quant-iT™ Protein Assay kit (Thermo Fisher Scientific Inc, USA) according to manufacturer's instructions. The Nanodrop ND3300 Quant-iT protocol at High-Range was used to produce the standard curve. Blank reading was performed using Quant-iT™ protein buffer.

2 µl of extracts were analysed and the reading was obtained as protein quantification (µg/mL). All promoter measurements were quantified as RFU/µg protein.

1.2. Results

Approximately 9 to 28 independent transgenic plant lines were generated for each promoter construct. Fluorometric measurements were made from wild-type tobacco and transgenic lines transformed with an 'empty' expression cassette with YPet reporter gene but no promoter sequence. This was done to analyse background fluorescence and promoter 'leakage' from the binary vector promoter expressing the antibiotic selection gene.

1.2.1. Fluorescence Screening with Handheld Flashlight

First round screening (whole plant analysis) was conducted using the Polilight FLARE flashlight. We started screening all the C1 (35S) and C2 (2×35S) plant lines of which the brightest lines were kept for fluorometric analysis. Plant lines that showed no or very low fluorescence were discarded. Fluoroscence spectroscopy revealed that the threshold brightness for plants to be discarded was approximately at less than 2 RFU/µg protein per transgenic line. Brightest C1 and C2 control plants were used for visual comparative analysis when transgenic plant lines of all the other promoter expression cassettes were screened with the Polilight.

1.3. Fluorescence Spectroscopy

Figure 2:
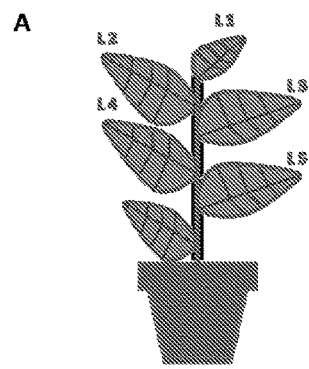
FIG. 2 shows a graphical representation of YPet reporter gene expression in 5 leaves analysed from 3 independent transgenic lines.
Figure 2:
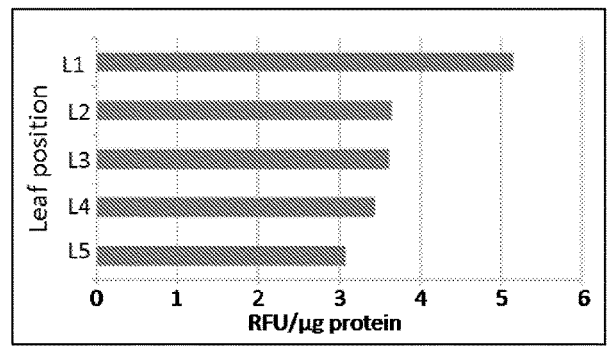
Figure 2:
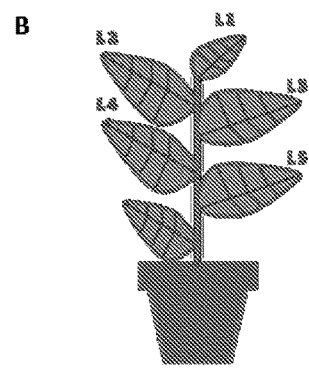
Figure 2:
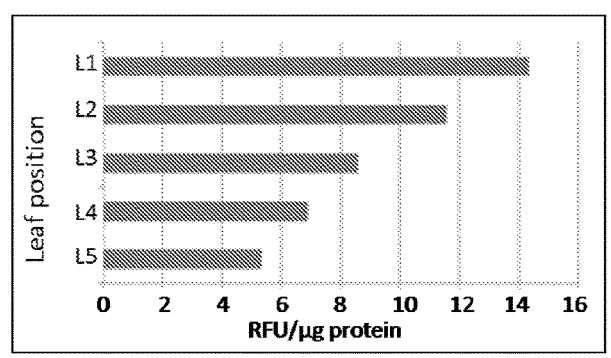
Figure 2:
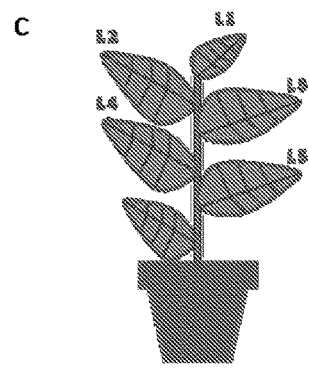
Figure 2:
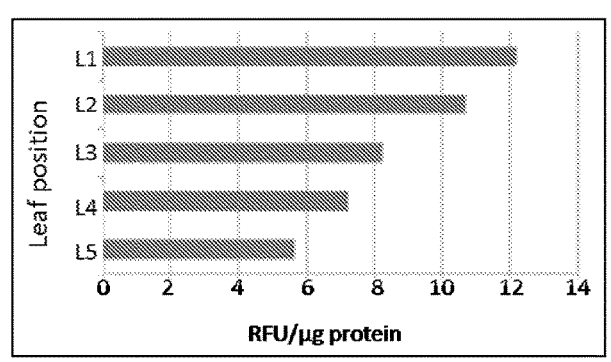

Initial results showed average promoter activity for each leaf position similar to Mitsuhara et al. 1996. All promoter constructs had similar expression profiles relative to leaf position (as illustrated in FIGS. 2A, B and C). However, on average, leaf size for positions L2, L3 and L4 were similar. Based on these profiles we selected the average expression data for leaf positions: L2, L3 and L4 for fluorometric analysis and comparison between all promoter constructs. The primary control promoter for comparative analysis was C2 (2×35S) of which a total of 27 transgenic plant lines were analyzed by fluorescence visulation and spectroscopy. Four promoters were identified as having the highest expression values ranging from 2.71 RFU/µg protein to a maximum of 4.34 RFU/µg protein.

Figure 3:
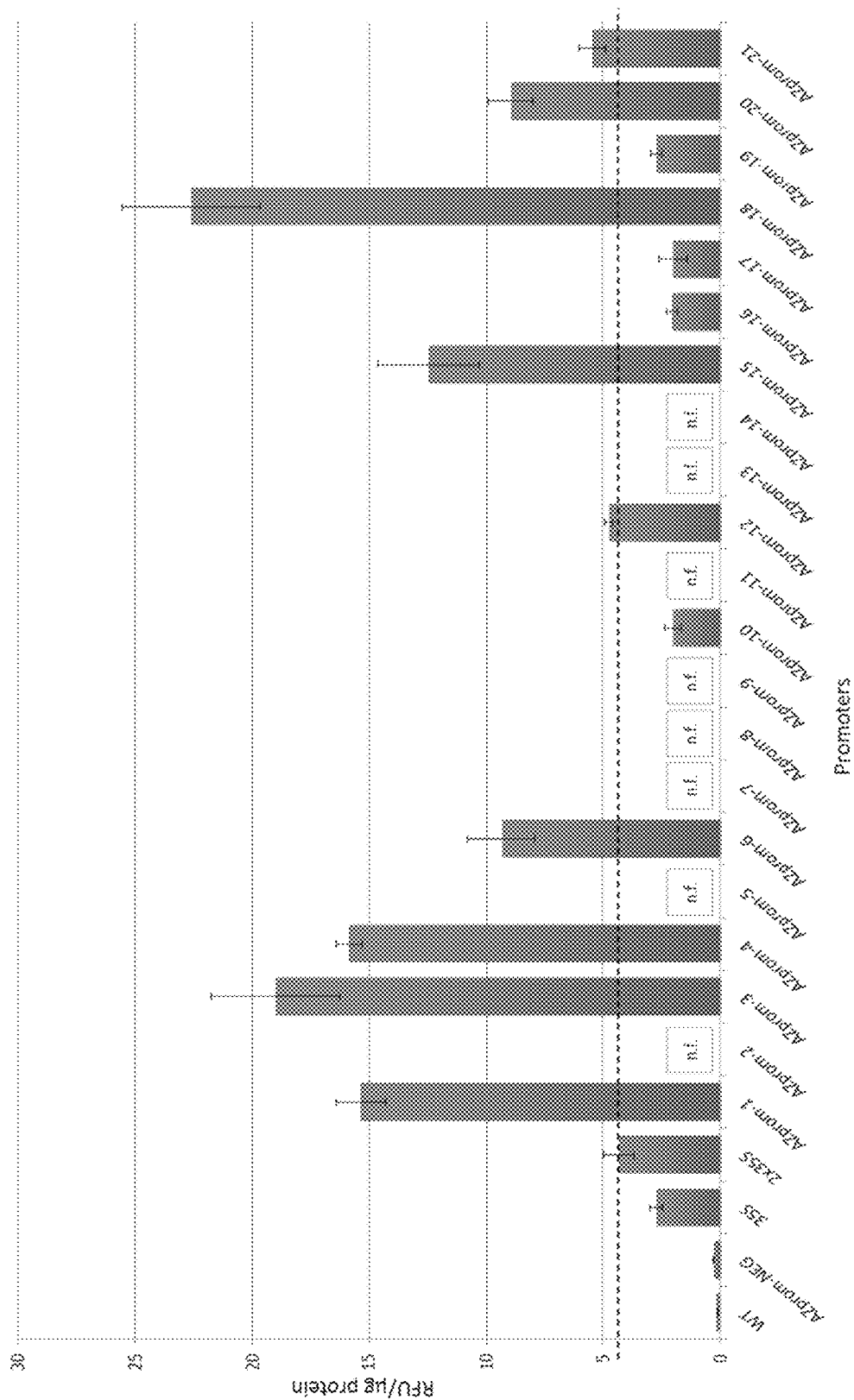
FIG. 3 shows a graphical representation of a comparison between all candidate synthetic promoter cassettes and the two control promoters (C1 and C2), showing transgenic lines of each promoter with the highest reporter gene expression. The dashed line represents the highest C2 (2×35S) fluorescence value measured (4.34 RFU/μg protein). Error bars show SE between three leaves per transgenic line measured. WT=wild-type, AZprom-NEG=promoterless negative control (empty vector').
Figure 4:
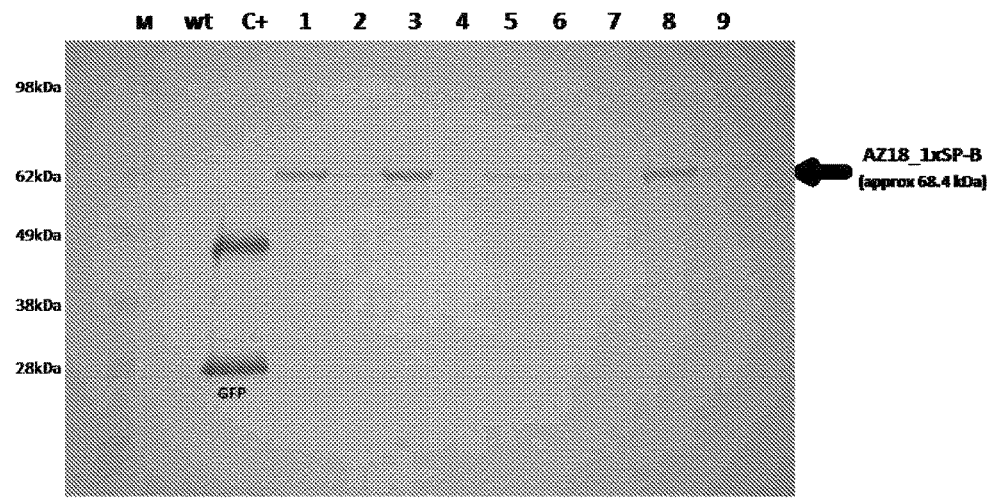
FIG. 4 shows a Western blot analysis for transgenic plant lines for AZ18_1×SP-B with the SeeBlue® Plus2 Pre-Stained protein standard (Life Technologies, LC5925).

All promoters were screened and transgenic plant lines (TO primary transformants) with the brightest YPet fluorescence of each candidate synthetic promoter cassette is illustrated in FIG. 3. Plant lines with candidate synthetic promoters discarded due to low (<2 RFU/µg protein) fluorescence are designated as 'n.f.' for 'no fluorescence'. A dashed line on the bar graph (FIG. 3) represents the highest C2 (2×35S) value. Transgenic plant lines represented also show the highest reporter gene values for each of the candidate synthetic promoter cassettes. As is evident from the graph AZprom-1, AZprom-3, AZprom-4 and AZprom-18 were the four candidate promoters that worked most efficiently compared with the C2 control. Table 3 indicates the PLACE database motifs identified in each of these four promoter cassettes.

Surprisingly, the AZprom-18 was found to have five times greater expression of the YPet transgene at the highest reporter gene value for a transgenic plant compared with the highest reporter gene value for a transgenic plant with the C2 control promoter. Furthermore, it was also one of the strongest overall synthetic promoters of which every transgenic plant tested had a YPet fluorescence level of above the 2 RFU/µg protein cut-off (Table 4).

Using the handheld Polilight flashlight, transgenic lines could be screened rapidly and lines from several synthetic promoters with overall low activity could be discarded after visual confirmation and comparison to the brightest fluorescence in C1 and C2 plant lines.

The four synthetic promoters AZprom-1, AZprom-3, AZprom-4 and AZprom-18, in particular AZprom-18, identified therefore show utility for use in plant genetic engineering strategies and biopharming applications.

TABLE 3

Motifs identified in selected promoter cassettes by PLACE database analysis

| MOTIF | POSITION from 5'-start to 3'-end (orientation + or −) |
|---|---|
| AZprom-1 | |
| PEA PLASTOCYANIN PROMOTER (609 bp) | |
| CACTFTPPCA1 | 19 (+) |
| CACTFTPPCA1 | 78 (−) |
| MYCCONSENSUSAT | 108 (+) |
| MYCCONSENSUSAT | 108 (−) |
| ASF1MOTIFCAMV1 | 68 (−) |
| MYCCONSENSUSAT | 171 (+) |
| MYCCONSENSUSAT | 171 (−) |
| MYCCONSENSUSAT | 224 (+) |
| MYCCONSENSUSAT | 224 (−) |
| CACTFTPPCA1 | 254 (−) |
| GATABOX | 278 (+) |
| GT1CONSENSUS | 436 (+) |
| GATABOX | 441 (−) |
| CACTFTPPCA1 | 455 (+) |
| CACTFTPPCA1 | 481 (−) |
| ATRICHPSPETE (SEQ ID NO: 39) | 496 (+) |
| CACTFTPPCA1 | 500 (+) |
| CACTFTPPCA1 | 504 (−) |
| CACTFTPPCA1 | 513 (+) |
| CCA1ATLHCB1 | 520 (+) |
| SORLIP1AT | 530 (+) |
| BOXIIPCCHS | 530 (−) |
| LTRECOREATCOR15 | 535 (−) |
| GATABOX | 542 (+) |
| IBOXCORE | 542 (+) |
| IBOXCORE | 581 (+) |
| CACTFTPPCA1 | 588 (+) |
| CACTFTPPCA1 | 603 (+) |

TABLE 3-continued

Motifs identified in selected promoter cassettes by PLACE database analysis

| MOTIF | POSITION from 5'-start to 3'-end (orientation + or −) |
|---|---|
| GRAPEVINE VPP PROMOTER (342 bp) | |
| RBCSCONSENSUS | 634 (−) |
| SORLIP1AT | 658 (−) |
| GT1CONSENSUS | 689 (+) |
| GT1CONSENSUS | 695 (+) |
| GT1CONSENSUS | 699 (−) |
| SORLREP2AT | 720 (−) |
| GT1MOTIFPSRBCS (SEQ ID NO: 41) | 741 (−) |
| GT1CONSENSUS | 743 (−) |
| INRNTPSADB | 746 (+) |
| CACTFTPPCA1 | 748 (+) |
| ASF1MOTIFCAMV | 759 (−) |
| GT1CONSENSUS | 763 (−) |
| IBOXCORE | 764 (−) |
| GATABOX | 765 (−) |
| ASF1MOTIFCAMV | 768 (−) |
| CACTFTPPCA1 | 777 (+) |
| CTRMCAMV35S | 780 (+) |
| CTRMCAMV35S | 782 (+) |
| CACTFTPPCA1 | 827 (−) |
| CACTFTPPCA1 | 847 (−) |
| INRNTPSADB | 850 (−) |
| SORLIP5AT | 851 (+) |
| CACTFTPPCA1 | 852 (−) |
| -10PEHVPSBD | 884 (+) |
| GATABOX | 905 (+) |
| GT1CONSENSUS | 913 (−) |
| LTREATLTI78 | 931 (−) |
| CBFHV | 932 (−) |
| DRECRTCOREAT | 932 (−) |
| LTRECOREATCOR15 | 932 (−) |
| AZprom-3 | |
| PEA PLASTOCYANIN PROMOTER (445 bp) X2 | |
| ASF1MOTIFCAMV | 4 (−) |
| MYCCONSENSUSAT | 7 (+) |
| MYCCONSENSUSAT | 7 (−) |
| MYCCONSENSUSAT | 60 (+) |
| MYCCONSENSUSAT | 60 (−) |
| CACTFTPPCA1 | 90 (−) |
| GATABOX | 114 (+) |
| GT1CONSENSUS | 272 (+) |
| GATABOX | 277 (−) |
| CACTFTPPCA1 | 291 (+) |
| CACTFTPPCA1 | 317 (−) |
| ATRICHPSPETE (SEQ ID NO: 39) | 332 (+) |
| CACTFTPPCA1 | 336 (+) |
| CACTFTPPCA1 | 340 (−) |
| CACTFTPPCA1 | 349 (+) |
| CCA1ATLHCB1 | 356 (+) |
| SORLIP1AT | 366 (+) |
| BOXIIPCCHS | 366 (−) |
| LTRECOREATCOR15 | 371 (−) |
| GATABOX | 378 (+) |
| IBOXCORE | 378 (+) |
| IBOXCORE | 417 (+) |
| CACTFTPPCA1 | 424 (+) |
| CACTFTPPCA1 | 439 (+) |
| ASF1MOTIFCAMV | 449 (−) |
| MYCCONSENSUSAT | 452 (+) |
| MYCCONSENSUSAT | 452 (−) |
| MYCCONSENSUSAT | 505 (+) |
| MYCCONSENSUSAT | 505 (−) |
| CACTFTPPCA1 | 535 (−) |
| GATABOX | 559 (+) |
| GT1CONSENSUS | 717 (+) |
| GATABOX | 722 (−) |
| CACTFTPPCA1 | 736 (+) |
| CACTFTPPCA1 | 762 (−) |
| ATRICHPSPETE (SEQ ID NO: 39) | 777 (+) |

TABLE 3-continued

Motifs identified in selected promoter cassettes by PLACE database analysis

| MOTIF | POSITION from 5'-start to 3'-end (orientation + or −) |
|---|---|
| CACTFTPPCA1 | 781 (+) |
| CACTFTPPCA1 | 785 (−) |
| CACTFTPPCA1 | 794 (+) |
| CCA1ATLHCB1 | 801 (+) |
| SORLIP1AT | 811 (+) |
| BOXIIPCCHS | 811 (−) |
| LTRECOREATCOR15 | 816 (−) |
| GATABOX | 823 (+) |
| IBOXCORE | 823 (+) |
| IBOXCORE | 862 (+) |
| CACTFTPPCA1 | 869 (+) |
| CACTFTPPCA1 | 884 (+) |
| CaMV 35S minimal promoter (98 bp) | |
| AS1CAMV (SEQ ID NO: 37) | 894 (+) |
| CACTFTPPCA1 | 895 (+) |
| ASF1MOTIFCAMV | 898 (+) |
| ASF1MOTIFCAMV | 910 (+) |
| CACTFTPPCA1 | 923 (+) |
| GATABOX | 926 (−) |
| INRNTPSADB | 961 (+) |
| MYCCONSENSUSAT | 968 (+) |
| MYCCONSENSUSAT | 968 (−) |
| Pea plastocyanin 5'-UTR (52b) as calculated from pea plastocyanin Transcriptional Start Site at −53 bp) | |
| CACTFTPPCA1 | 1007 (−) |
| CACTFTPPCA1 | 1025 (+) |
| GT1CONSENSUS | 1034 (+) |
| AZprom-4 | |
| PEA PLASTOCYANIN PROMOTER (445 bp) X2 | |
| ASF1MOTIFCAMV | 4 (−) |
| MYCCONSENSUSAT | 7 (+) |
| MYCCONSENSUSAT | 7 (−) |
| MYCCONSENSUSAT | 60 (+) |
| MYCCONSENSUSAT | 60 (−) |
| CACTFTPPCA1 | 90 (+) |
| GATABOX | 114 (+) |
| GT1CONSENSUS | 272 (+) |
| GATABOX | 277 (−) |
| CACTFTPPCA1 | 291 (+) |
| CACTFTPPCA1 | 317 (−) |
| ATRICHPSPETE (SEQ ID NO: 39) | 332 (+) |
| CACTFTPPCA1 | 336 (+) |
| CACTFTPPCA1 | 340 (−) |
| CACTFTPPCA1 | 349 (+) |
| CCA1ATLHCB1 | 356 (+) |
| SORLIP1AT | 366 (+) |
| BOXIIPCCHS | 366 (−) |
| LTRECOREATCOR15 | 371 (−) |
| GATABOX | 378 (+) |
| IBOXCORE | 378 (+) |
| IBOXCORE | 417 (+) |
| CACTFTPPCA1 | 424 (+) |
| CACTFTPPCA1 | 439 (+) |
| ASF1MOTIFCAMV | 449 (−) |
| MYCCONSENSUSAT | 452 (+) |
| MYCCONSENSUSAT | 452 (−) |
| MYCCONSENSUSAT | 505 (+) |
| MYCCONSENSUSAT | 505 (−) |
| CACTFTPPCA1 | 535 (−) |
| GATABOX | 559 (+) |
| GT1CONSENSUS | 717 (+) |
| GATABOX | 722 (−) |
| CACTFTPPCA1 | 736 (+) |
| CACTFTPPCA1 | 762 (−) |
| ATRICHPSPETE (SEQ ID NO: 39) | 777 (+) |
| CACTFTPPCA1 | 781 (+) |
| CACTFTPPCA1 | 785 (−) |
| CACTFTPPCA1 | 794 (+) |
| CCA1ATLHCB1 | 801 (+) |
| SORLIP1AT | 811 (+) |
| BOXIIPCCHS | 811 (−) |
| LTRECOREATCOR15 | 816 (−) |
| GATABOX | 823 (+) |
| IBOXCORE | 823 (+) |
| IBOXCORE | 862 (+) |
| CACTFTPPCA1 | 869 (+) |
| CACTFTPPCA1 | 884 (+) |
| GRAPEVINE VPP PROMOTER (342 bp) | |
| RBCSCONSENSUS | 915 (−) |
| SORLIP1AT | 939 (−) |
| GT1CONSENSUS | 970 (+) |
| GT1CONSENSUS | 976 (+) |
| GT1CONSENSUS | 980 (−) |
| SORLREP2AT | 1001 (−) |
| GT1MOTIFPSRBCS (SEQ ID NO: 41) | 1022 (−) |
| GT1CONSENSUS | 1024 (−) |
| INRNTPSADB | 1027 (+) |
| CACTFTPPCA1 | 1029 (+) |
| ASF1MOTIFCAMV | 1040 (−) |
| GT1CONSENSUS | 1044 (−) |
| IBOXCORE | 1045 (−) |
| GATABOX | 1046 (−) |
| ASF1MOTIFCAMV | 1049 (−) |
| CACTFTPPCA1 | 1058 (+) |
| CTRMCAMV35S | 1061 (+) |
| CTRMCAMV35S | 1063 (+) |
| CACTFTPPCA1 | 1108 (−) |
| CACTFTPPCA1 | 1128 (−) |
| INRNTPSADB | 1131 (−) |
| SORLIP5AT | 1132 (+) |
| CACTFTPPCA1 | 1133 (−) |
| -10PEHVPSBD | 1165 (+) |
| GATABOX | 1186 (+) |
| GT1CONSENSUS | 1194 (−) |
| LTREATLTI78 | 1212 (−) |
| CBFHV | 1213 (−) |
| DRECRTCOREAT | 1213 (−) |
| LTRECOREATCOR15 | 1213 (−) |
| AZprom-18 | |
| Ath cab2 selected region (115 bp) X2 | |
| LRENPCABE | 18 (−) |
| SORLIP1AT | 19 (+) |
| BOXIIPCCHS | 19 (−) |
| CACTFTPPCA1 | 31 (+) |
| GATABOX | 39 (+) |
| GT1CONSENSUS | 39 (+) |
| IBOXCORE | 39 (+) |
| CCA1ATLHCB1 | 47 (+) |
| RBCSCONSENSUS | 58 (+) |
| CGF1ATCAB2 (SEQ ID NO: 45) | 75 (+) |
| GATABOX | 75 (+) |
| GT1CONSENSUS | 75 (+) |
| IBOXCORE | 75 (+) |
| CACTFTPPCA1 | 84 (+) |
| GATABOX | 91 (+) |
| GATABOX | 110 (−) |
| LRENPCABE | 133 (−) |
| SORLIP1AT | 134 (+) |
| BOXIIPCCHS | 134 (−) |
| CACTFTPPCA1 | 146 (+) |
| GATABOX | 154 (+) |
| GT1CONSENSUS | 154 (+) |
| IBOXCORE | 154 (+) |
| CCA1ATLHCB1 | 162 (+) |
| RBCSCONSENSUS | 173 (+) |
| CGF1ATCAB2 (SEQ ID NO: 45) | 190 (+) |
| GATABOX | 190 (+) |
| GT1CONSENSUS | 190 (+) |

TABLE 3-continued

Motifs identified in selected promoter cassettes by PLACE database analysis

| MOTIF | POSITION from 5'-start to 3'-end (orientation + or −) |
|---|---|
| IBOXCORE | 190 (+) |
| CACTFTPPCA1 | 199 (+) |
| GATABOX | 206 (+) |
| GATABOX | 225 (−) |
| Ath cab2 promoter region (−564 relative to start codon) | |
| ASF1MOTIFCAMV | 237 (−) |
| GATABOX | 254 (+) |
| GATABOX | 256 (−) |
| CIACADIANLELHC (SEQ ID NO: 40) | 273 (−) |
| GATABOX | 290 (+) |
| GT1CONSENSUS | 290 (+) |
| IBOXCORE | 290 (+) |
| CACTFTPPCA1 | 295 (−) |
| ASF1MOTIFCAMV | 297 (+) |
| CACTFTPPCA1 | 335 (−) |
| GT1CONSENSUS | 350 (−) |
| GT1CONSENSUS | 359 (+) |
| GATABOX | 368 (+) |
| GT1CONSENSUS | 382 (+) |
| CACTFTPPCA1 | 403 (+) |
| GT1CONSENSUS | 438 (−) |
| CACTFTPPCA1 | 453 (+) |
| CACTFTPPCA1 | 510 (−) |
| CACTFTPPCA1 | 514 (−) |
| CACTFTPPCA1 | 528 (−) |
| CACTFTPPCA1 | 535 (−) |
| SORLIP1AT | 536 (−) |
| GT1CONSENSUS | 576 (+) |
| MYCCONSENSUSAT | 589 (+) |
| MYCCONSENSUSAT | 589 (+) |
| LRENPCABE | 611 (−) |
| SORLIP1AT | 612 (+) |
| BOXIIPCCHS | 612 (−) |
| CACTFTPPCA1 | 624 (+) |
| GATABOX | 632 (+) |
| GT1CONSENSUS | 632 (+) |
| IBOXCORE | 632 (+) |
| CCA1ATLHCB1 | 640 (+) |
| RBCSCONSENSUS | 651 (+) |
| CGF1ATCAB2 (SEQ ID NO: 45) | 668 (+) |
| GATABOX | 668 (+) |
| GT1CONSENSUS | 668 (+) |
| IBOXCORE | 668 (+) |
| CACTFTPPCA1 | 677 (+) |
| GATABOX | 684 (+) |
| GATABOX | 703 (−) |
| RBCSCONSENSUS | 714 (+) |
| CIACADIANLELHC (SEQ ID NO: 40) | 718 (+) |
| CACTFTPPCA1 | 721 (+) |
| GATABOX | 724 (−) |
| CACTFTPPCA1 | 742 (+) |
| SORLIP5AT | 746 (−) |
| CACTFTPPCA1 | 748 (+) |

TABLE 4

Number and percentage of transgenic plant lines positive for YPet fluorescence above the 2 RFU/μg protein cut-off

| Total No of plant lines | Promoter | Fluorescence spectroscopy +ve | % |
|---|---|---|---|
| 19 | C1 (35S) | 9 | 47 |
| 27 | C2 (2 × 35S) | 12 | 44 |
| 12 | AZprom-1 | 4 | 33 |
| 9 | AZprom-2 | 0 | / |
| 21 | AZprom-3 | 14 | 67 |
| 27 | AZprom-4 | 7 | 26 |
| 13 | AZprom-5 | 0 | / |
| 27 | AZprom-6 | 2 | 7 |
| 28 | AZprom-7 | 0 | / |
| 11 | AZprom-8 | 0 | / |
| 10 | AZprom-9 | 0 | / |
| 24 | AZprom-10 | 1 | 4 |
| 10 | AZprom-11 | 0 | / |
| 25 | AZprom-12 | 11 | 44 |
| 10 | AZprom-13 | 0 | / |
| 10 | AZprom-14 | 0 | / |
| 10 | AZprom-15 | 1 | 10 |
| 25 | AZprom-16 | 3 | 12 |
| 10 | AZprom-17 | 2 | 20 |
| 12 | AZprom-18 | 12 | 100 |
| 20 | AZprom-19 | 1 | 5 |
| 10 | AZprom-20 | 4 | 40 |
| 13 | AZprom-21 | 6 | 46 |

Example 2

2.1. Materials and Methods 2.1.1. Expression of Two Fusion Proteins Using Synthetic Promoter AZprom 18

The expression cassette within ImpactVector 1.1 comprising the AZprom_18 [SEQ NO. 18] synthetic promoter was modified by replacing the single gene coding for YPet fluorescent protein with cDNA coding for: (i) YPet—linker1—TEV cleavage site—single copy of human mature (8 kDa) pulmonary surfactant protein SP-B peptide [SEQ ID NO: 29]—TEV cleavage site—linker2—YPet (AZ18_1× SP-B) [SEQ ID NO: 30]; or (ii) YPet—linker1—TEV cleavage site—double copy of human mature (8 kDa) pulmonary surfactant protein SP-B peptide [SEQ ID NO: 29]—TEV cleavage site—linker2—YPet (AZ18_2×SP-B) [SEQ ID NO: 31]. The modified AZprom_18 promoter expression cassettes were then excised and sub-cloned in a binary vector, pCAMBIA, suitable for Agrobacterium-mediated plant transformation.

2.1.2. Generation of Transgenic Plants and Fluorescence Screening

Tobacco plants (Nicotiana tabacum var Samsun) were maintained on MS medium in a temperature (22° C.) regulated growth room at a 16 h photoperiod. The pCAMBIA expression vectors comprising fusion cassettes AZ18_1× SP-B and AZ18_2×SP-B were introduced into Agrobacterium tumefaciens strain LBA4404 via electroporation [Mattanovich et al 1989] followed by plant transformation using a standard leaf disc method [Horsch et al 1985]. Tobacco plantlets were regenerated under kanamycin selection on MS medium and primary transgenic plantlets were hardened off and grown in a containment glasshouse under standard glasshouse conditions at 22° C. To evaluate transgenic status of tobacco plants, plantlets were screened using a handheld ROFIN Polilight FLARE PLUS 2 forensic flashlight (ROFIN forensics, Australia) with a Cyan LED output of 485 nm to 515 nm and orange filter goggles with a range of 190 nm to 545 nm. Plantlets showing fluorescence were transferred to the growth room and were continuously screened for 8 to 12 weeks.

2.1.3. Protein Extraction and Western Blot Analysis

Proteins were extracted from the plant tissue with a buffer containing 1× phosphate buffered saline (PBS, Sigma-Aldrich, 79383) with 7M Urea, 2M Thiourea, 5% CHAPS and 5% 2-mercaptoethanol. 500 mg of plant leaf material that was ground up in liquid Nitrogen was extracted with 1 ml of extraction buffer. The extract was vortexed for 1 min and left on the bench for 10 minutes where after it was vortexed again and centrifuged for 10 min at 13000×g. The supernatant was used directly to load into the gel for western blot analysis. SDS PAGE was performed with the Life technologies Bolt™ system (Life Technologies) using Bis-Tris MOPS buffer and 4-12% gradient gel. Transfer and western blot was performed with the Life technologies iBlot® system according to the instructions of the manufacturer. Chromogenic detection was done using the iBlot® chromogenic western detection kit (Life Technologies, IB7410-01). All transgenic plant lines from AZ18_1×SP-B and AZ18_2×SP-B were screened with an antibody specific for GFP mutants (Thermo Fischer Scientific, PA1-28521). To serve as a positive control, fluorescent protein (YPet) was extracted from transgenic plants transformed with promoter expression cassette C2 (2×35S).

2.2. Results & Discussion 2.2.1. Western Blot Analysis

Figure 5:
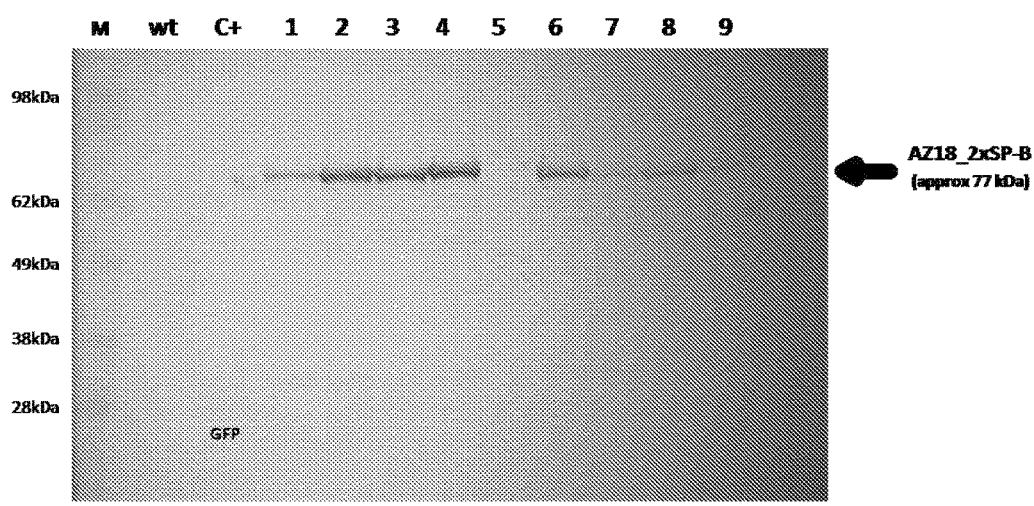
FIG. 5 shows a Western blot analysis for transgenic plant lines for AZ18_2×SP-B with the SeeBlue® Plus2 Pre-Stained protein standard (Life Technologies, LC5925).

Western blot analysis showed positive detection of the GFP antibody in several transgenic plant lines for both AZ18_1×SP-B and AZ18_2×SP-B at the expected fusion protein size when compared to the SeeBlue® Plus2 Pre-Stained protein standard (Life Technologies, LC5925) as noted in FIG. 5 and FIG. 6 respectively. GFP antibody detects positive control, fluorescent protein (YPet), at approximately 28 kDa. Detection of GFP positive control in FIG. 5 was faint, but visible. Detection of GFP positive control in FIG. 6 was strong, but also showed detection of a larger fragment which could be due to formation of a YPet dimer complex. Nine (9) independent plant lines were analysed for each AZ18-expression cassette. Western blot analysis for AZ18_1×SP-B showed GFP antibody detection at the expected size of approximately 68.4 kDa for 7 transgenic lines (FIG. 5) and AZ18_2×SP-B showed GFP antibody detection at the expected size of approximately 77 kDa for 8 transgenic lines (FIG. 6).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Benfey P N, Ren L, Chua N-H (1990) Combinatorial and synergistic properties of CaMV 35S enhancer subdomains. EMBO J 9:1685-1696

Bhullar S, Chakravarthy S, Advani S, Datta S, Pental D, Kumar Burma P (2003) Strategies for development of functionally equivalent promoters with minimum sequence homology for transgene expression in plants: cis-elements in a novel DNA context versus domain swapping. Plant Physiol 132:988-998

Bhullar S, Datta S, Advani S, Chakravarthy S, Gautam T, Pental D, Kumar Burma P (2007) Functional analysis of the cauliflower mosaic virus 35S promoter: re-evaluation of the role of subdomains B5, B4, and B2 in promoter activity. Plant Biotechnol J 5:696-708

Higo, K., Y. Ugawa, M. Iwamoto and T. Korenaga (1999) Plant cis-acting regulatory DNA elements (PLACE) database:1999. Nucleic Acids Research Vol. 27 No. 1 pp. 297-300.

Horsch R, Fry J, Hofmann N, Eichhlotz D, Rogers S, Frayley R (1985) A simple and general method for transferring genes into plants. Science 227(4691): 1229-1231

Lescot M, Déhais P, Thijs G, Marchal K, Moreau Y, Van de Peer Y, Rousé P and Rombauts S (2002) PlantCARE, a database of plant cis-acting refulatory elements and a portal to tools for in silico analysis of promoter sequences. Nucleic Acids Research 30(1):325-327

Mattanovich D, Ruker F, da Camara Machado A, Laimer M, Regner F, Steinkeliner H, Himmler G, Katinger H (1989) Efficient transformation of *Agrobacterium* spp. by eletroporation. Nucleic Acids Research 17(16):6747

Mitsuhara I, Ugaki M, Hirochika H, Ohshima M, Murakami T, Gotoh Y, Katayose Y, Nakamura S, Honkura R, Nishimiya S, Ueno K, Mochizuki A, Tanimoto H, Tsugawa H, Otsuki Y, Ohashi Y (1996) Efficient promoter cassettes for enhanced expression of foreign genes in dicotyledonous and monocotyledonous plants. Plant Cell Physiol 37:49-59.

Benfey and Chua N-H (1990) The cauliflower mosaic virus 35S promoter: Combinatorial regulation of transcription in plants. Science 250: 959-966

Pryhuber G S (1998) Regulation and function of pulmonary surfactant protein B. Molecular Genetics and Metabolism 64: 217-228

Venter M (2007) Synthetic promoters: genetic control through cis engineering. Trends Plant Sci. 12, 118-124

Venter M & Botha F C (2010) in Plant Developmental Biology—Biotechnological Perspectives Vol. 2 (eds Pua, E. C. & Davey, M. R.) 393-408 (Springer).

What is claimed is:

1. An isolated polynucleotide comprising a regulatory nucleic acid sequence (a) having at least 95% or more sequence identity to a polynucleotide sequence set forth in any one of SEQ ID NOs: 1, 3, 4 or 18, wherein
   (A) the regulatory nucleic acid sequence contains the following motifs:
   ASF1MOTIFCAMV (TGACG),
   CTRMCAMV35S (TCTCTCTCT),
   MYCCONSENSUSAT (CANNTG),
   SORLIP1AT (GCCAC),
   BOXIIPCCHS (ACGTGGC),
   CCA1ATLHCB1 (AA(C/A)AATCT),
   GT1CONSENSUS (G(A/G)(A/T)AA(A/T),
   IBOXCORE (GATAA),
   GATABOX (GATA), and
   CACTFTPPCA1 ((T/C)ACT); and
   (B) wherein the regulatory nucleic acid sequence having at least 95% or more sequence identity to a polynucleotide sequence set forth in any one of SEQ ID NOs: 1, 4 or 18 further contains the following motifs:
   SORLIP5AT (GAGTGAG), and
   RBCSCONSENSUS (AATCCAA); and
   (C) wherein the regulatory nucleic acid sequence having at least 95% or more sequence identity to a polynucleotide sequence set forth in any one of SEQ ID NOs: 1, 3 or 4 further contains the following motifs:
   INRNTPSADB ((C/T)TCANT(C/T)(C/T)),
   ATRICHPSPETE (AATATACTAGTATTATT-TACTAAAAAAAATC [SEQ ID NO: 39]), and
   LTRECOREATCOR15 (CCGAC); and
   (D) wherein the regulatory nucleic acid sequence having at least 95% or more sequence identity to a polynucleotide sequence set forth in any one of SEQ ID NOs: 1 or 4 further contains the following motifs:
   SORLREP2AT (ATAAAACGT),
   GT1MOTIFPSRBCS ((G/T)(A/T)GTG(A/G)(A/T)AA(A/T)(A/G)(A/T) [SEQ ID NO: 41]), -10PEHVPSBD (TATTCT),
LTREATLTI78 (ACCGACA),
CBFHV ((A/G)(C/T)CCGAC), and
DRECRTCOREAT ((A/G)CCGAC); and
(E) wherein the regulatory nucleic acid sequence having at least 95% or more sequence identity to a polynucleotide sequence set forth in SEQ ID NO: 4 further contains the motif AS1CAMV (CCACTGACGTAAGGGATGACGCACAATCC [SEQ ID NO: 37]); and
(F) wherein the regulatory nucleic acid sequence having at least 95% or more sequence identity to a polynucleotide sequence set forth in SEQ ID NO: 18 further contains the following motifs:
LRENPCABE (ACGTGGCA), SORLIP1AT (GCCAC), CGF1ATCAB2 (GATAAAGATTACTTCAGATATAACAAACGTTAC [SEQ ID NO 45]), and
CIACADIANLELHC (CAANNNNATC [SEQ ID NO: 40]).

2. The isolated polynucleotide according to claim 1, further comprising one or more restriction enzyme sites for inserting a second nucleic acid sequence heterologous to the regulatory nucleic acid sequence into the polynucleotide, such that the inserted second nucleic acid sequence would be operably linked to the regulatory nucleic acid sequence, wherein the regulatory nucleic acid sequence is capable of directing transcription of the second operably linked nucleic acid sequence.

3. The isolated polynucleotide according to claim 2, comprising the second nucleic acid sequence, wherein the second nucleic acid sequence encodes a target protein heterologous to the regulatory nucleic acid sequence and is operably linked to the regulatory nucleic acid sequence.

4. The isolated polynucleotide according to claim 1, wherein the regulatory nucleic acid sequence has at least 95%, 96%, 97%, 98%, 99%, or 100% sequence identity to any one of SEQ ID NOs: 1, 3, 4 or 18.

5. The isolated polynucleotide according to claim 3, wherein the second nucleotide sequence encodes a target protein useful in the food or beverage industries, the pharmaceutical industry, in agriculture, or in the chemical industry.

6. The isolated polynucleotide according to claim 3, wherein the second nucleotide sequence encodes a therapeutic protein.

7. The isolated polynucleotide according to claim 3, wherein the second nucleotide sequence encodes one or more copies of: (A) a pulmonary surfactant protein-B (SP-B) pre-proprotein or a functional fragment or analog thereof; (B) SP-B mature peptide or a functional fragment or analog thereof; or (C) both (A) and (B).

8. The isolated polynucleotide according to claim 1, further comprising a polynucleotide sequence encoding a signal peptide selected from the group consisting of the signal peptide region of equistatin and of *Nicotiana tabacum* thionin (NtSP).

9. The isolated polynucleotide according to claim 1, further comprising a polynucleotide sequence encoding a trafficking peptide selected from the group consisting of an endoplasmic reticulum (ER)-trafficking peptide; an oil body-trafficking peptide, a protein storage vacuole-trafficking peptide; and a plastid-trafficking peptide.

10. The isolated polynucleotide according to claim 1, further comprising a polynucleotide sequence encoding a tag selected from the group consisting of polyhistidine, Leptin, late embryogenesis abundant protein (LEA), Lectin, maltose binding protein (MBP) and glutathione S-transferase (GST).

11. The isolated polynucleotide according to claim 1, further comprising a polynucleotide sequence encoding a marker protein for detection, selected from the group consisting of yellow fluorescent protein (YPet), green fluorescent protein (GFP), chloramphenicol acetyl transferase (CAT), and luciferase.

12. The isolated polynucleotide according to claim 1, further comprising a polynucleotide sequence encoding a protease cleavage site, selected from the group consisting of an enterokinase, a chymosin and a Tobacco Etch Virus (TEV) protease cleavage site.

13. The isolated polynucleotide according to claim 1, further comprising a psbA regulatory 5'-UTR and 3' UTR region for targeting a plastid.

14. An expression cassette for expression of a protein in a plant comprising the isolated polynucleotide according to claim 1.

15. The expression cassette according to claim 14, comprising one or more restriction enzyme sites for inserting a second nucleic acid sequence heterologous to the regulatory nucleic acid sequence into the polynucleotide, such that the inserted second nucleic acid sequence would be operably linked to the regulatory nucleic acid sequence, wherein the regulatory nucleic acid sequence is capable of directing transcription of the second operably linked nucleic acid sequence.

16. The expression cassette according to claim 15, wherein the expression cassette comprises the second nucleic acid sequence, and wherein the second nucleic acid sequence encodes a target protein heterologous to the regulatory nucleic acid sequence and is operably linked to the regulatory nucleic acid sequence.

17. The expression cassette according to claim 16, wherein the second nucleotide sequence encodes one or more copies of: (A) a pulmonary surfactant protein-B (SP-B) pre-proprotein or a functional fragment or analog thereof; (B) SP-B mature peptide or a functional fragment or analog thereof; or (C) both (A) and (B).

18. The expression cassette according to claim 14, further comprising any one or more elements from the group consisting of:
  (i) a polynucleotide sequence encoding a signal peptide from the group consisting of the signal peptide region of equistatin and of *Nicotiana tabacum* thionin (NtSP);
  (ii) a polynucleotide sequence encoding a trafficking peptide from the group consisting of an endoplasmic reticulum (ER)-trafficking peptide; an oil body-trafficking peptide, a protein storage vacuole-trafficking peptide; and a plastid-trafficking peptide;
  (iii) a polynucleotide sequence encoding a tag from the group consisting of polyhistidine, Leptin, late embryogenesis abundant protein (LEA), Lectin, maltose binding protein (MBP) and glutathione S-transferase (GST);
  (iv) a polynucleotide sequence encoding a marker protein for detection from the group consisting of yellow fluorescent protein (YPet), green fluorescent protein (GFP), chloramphenicol acetyl transferase (CAT), and luciferase;
  (v) a polynucleotide sequence encoding a protease cleavage site from the group consisting of an enterokinase, a chymosin and a Tobacco Etch Virus (TEV) protease cleavage site; and
  (vi) a psbA regulatory 5'-UTR and 3' UTR region for targeting a plastid.

19. A plant cell comprising the isolated polynucleotide according to claim 3.

20. A method of expressing a target protein in a plant comprising introducing the isolated polynucleotide according to claim 3 into a plant cell, and expressing the target protein in the plant cell.

21. The method according to claim 20, further comprising a step of exposing the plant cell to one or more induction stimuli.

22. The method according to claim 21, wherein the one or more induction stimuli are selected from the group consisting of different intensities and periods of light exposure, cold shock, heat shock, induction of drought conditions and hormone induction.

23. The method of claim 22, wherein the hormone induction comprises induction with Abscisic Acid (ABA).

* * * * *

SEQUENCE LISTING

```
<160> NUMBER OF SEQ ID NOS: 45

<210> SEQ ID NO 1
<211> LENGTH: 951
<212> TYPE: DNA
<213> ORGANISM: Artificial Sequence
<220> FEATURE:
<223> OTHER INFORMATION: AZprom_1 synthetic promoter

<400> SEQUENCE: 1
tatgcaactt acaacgtgca ctcgcggagg attggacgtg tgcaacttac aacgtacgca    60
```

-continued

```
ttgttcgttc atacaatagt gtagaattgg agatgtgcaa cttacaacat gtgcaactta      120
caacgtgcgc tcgcggagga atgtgaagtt gaacacgtac aaacttacgt catttgtgca      180
tgcagaagca tagagctgag cacacaattc ataatttgaa ggacacatga tttgctataa      240
agaactcttt agaagtacca caactttgac tgagtttgat atagctaata aagatggagc      300
tcattataat ttgaatggca taatgcaagc taaacgaaca agcttagtta atcatgttaa      360
acaacaattc tttgtaataa taaaattgtc tttcaactag tccaagttta tgagttgatt      420
cttcggaata aattagaaaa tatcttagat tttatacttc attgattatt tcatagagca      480
agtaggagaa ataaaaatat actagtatta tttactaaaa aaaatctaag ccacgtcgga      540
ggataacatc caacccagcc aatcacagca atgttcatca gataacccac tttaagccca      600
cgcactctga gatccaaaaa tggttgagct gttttggatt tggcaattaa ttgcatcgtg      660
gcaacgtgga attaacaaaa atggagctgg aaatggtaat tttcaaaaat attttgtaaa      720
cgttttataa taatagaatt atttttcac tctctcatcg tcattatcgt catcatcact      780
ctctctctct acgcttgcat atatataaac cattgcagag ccgcggagtg tcaagcatcg      840
tggtggagta gagtgagaga accgaagcca aaggcaactc cattattctc tctcgtgttc      900
tcgtgatatt ggttttccgg cgccggagct tgtcggtccg tccgtccgtc c             951
```

<210> SEQ ID NO 2
<211> LENGTH: 1149
<212> TYPE: DNA
<213> ORGANISM: Artificial Sequence
<220> FEATURE:
<223> OTHER INFORMATION: AZprom_2 synthetic promoter
<400> SEQUENCE: 2

```
atcgaatttg ttgggcaagc gcccagtgtg atgtacgttg ggaaaacttg caagaggatg       60
cgaccaaatg aactggtaaa ccatcccgtg agcgtggcct acacatttta agccagcggt      120
ctctttcgac ttgtcttaca aaagctggtc cagtcacgag ccttagccct aaccatagcc      180
acaagtacat ctcatccatt taaggcctct gcgtgcacca atggcatcca agctgcagat      240
ttcttttcac caccgtctct cttgtcagca tcgaatttgt tgggcaagcg cccagtgtga      300
tgtacgttgg gaaaacttgc aagaggatgc gaccaaatga actggtaaac catcccgtga      360
gcgtggccta cacattttaa gccagcggtc tctttcgact tgtcttacaa aagctggtcc      420
agtcacgagc cttagcccta accatagcca agtacatc tcatccattt aaggcctctg      480
cgtgcaccaa tggcatccaa gctgcagatt cttttcacc accgtctctc ttgtcagcat      540
cgaatttgtt gggcaagcgc ccagtgtgat gtacgttggg aaaacttgca agaggatgcg      600
accaaatgaa ctggtaaacc atcccgtgag cgtggcctac acattttaag ccagcggtct      660
ctttcgactt gtcttacaaa agctggtcca gtcacgagcc ttagccctaa ccatagccac      720
aagtacatct catccattta aggcctctgc gtgcaccaat ggcatccaag ctgcagattt      780
cttttcacca ccgtctctct tgtcagcaga tccaaaaatg gttgagctgt tttggatttg      840
gcaattaatt gcatcgtggc aacgtggaat taacaaaaat ggagctggaa atggtaattt      900
tcaaaaatat tttgtaaacg ttttataata atagaattat tttttcactc tctcatcgtc      960
attatcgtca tcatcactct ctctctctac gcttgcatat atataaacca ttgcagagcc     1020
gcggagtgtc aagcatcgtg gtggagtaga gtgagagaac cgaagccaaa ggcaactcca     1080
ttattctctc tcgtgttctc gtgatattgg ttttccggcg ccggagcttg tcggtccgtc     1140
cgtccgtcc                                                            1149
```

<210> SEQ ID NO 3
<211> LENGTH: 1039
<212> TYPE: DNA
<213> ORGANISM: Artificial Sequence
<220> FEATURE:
<223> OTHER INFORMATION: AZprom_3 synthetic promoter

<400> SEQUENCE: 3

```
ttacgtcatt tgtgcatgca gaagcataga gctgagcaca caattcataa tttgaaggac      60
acatgatttg ctataaagaa ctctttagaa gtaccacaac tttgactgag tttgatatag     120
ctaataaaga tggagctcat tataatttga atggcataat gcaagctaaa cgaacaagct     180
tagttaatca tgttaaacaa caattctttg taataataaa attgtctttc aactagtcca     240
agtttatgag ttgattcttc ggaataaatt agaaaatatc ttagatttta tacttcattg     300
attatttcat agagcaagta ggagaaataa aaatatacta gtattattta ctaaaaaaaa     360
tctaagccac gtcggaggat aacatccaac ccagccaatc acagcaatgt tcatcagata     420
acccactttta agcccacgca ctctgttacg tcatttgtgc atgcagaagc atagagctga     480
gcacacaatt cataatttga aggacacatg atttgctata agaactctt tagaagtacc     540
acaactttga ctgagtttga tatagctaat aaagatggag ctcattataa tttgaatggc     600
ataatgcaag ctaaacgaac aagcttagtt aatcatgtta acaacaatt ctttgtaata     660
ataaaattgt ctttcaacta gtccaagttt atgagttgat tcttcggaat aaattagaaa     720
atatcttaga ttttatactt cattgattat ttcatagagc aagtaggaga ataaaaata     780
tactagtatt atttactaaa aaaaatctaa gccacgtcgg aggataacat ccaacccagc     840
caatcacagc aatgttcatc agataaccca ctttaagccc acgcactctg tctccactga     900
cgtaagggat gacgcacaat cccactatcc ttcgcaagac ccttcctcta tataaggaag     960
ttcatttcat ttggagagga cacgctgttc aaacacatac aaattcagta gagaagaaac    1020
tcattactct tgagaaaaa                                                  1039
```

<210> SEQ ID NO 4
<211> LENGTH: 1232
<212> TYPE: DNA
<213> ORGANISM: Artificial Sequence
<220> FEATURE:
<223> OTHER INFORMATION: AZprom_4 synthetic promoter

<400> SEQUENCE: 4

```
ttacgtcatt tgtgcatgca gaagcataga gctgagcaca caattcataa tttgaaggac      60
acatgatttg ctataaagaa ctctttagaa gtaccacaac tttgactgag tttgatatag     120
ctaataaaga tggagctcat tataatttga atggcataat gcaagctaaa cgaacaagct     180
tagttaatca tgttaaacaa caattctttg taataataaa attgtctttc aactagtcca     240
agtttatgag ttgattcttc ggaataaatt agaaaatatc ttagatttta tacttcattg     300
attatttcat agagcaagta ggagaaataa aaatatacta gtattattta ctaaaaaaaa     360
tctaagccac gtcggaggat aacatccaac ccagccaatc acagcaatgt tcatcagata     420
acccactttta agcccacgca ctctgttacg tcatttgtgc atgcagaagc atagagctga     480
gcacacaatt cataatttga aggacacatg atttgctata agaactctt tagaagtacc     540
acaactttga ctgagtttga tatagctaat aaagatggag ctcattataa tttgaatggc     600
ataatgcaag ctaaacgaac aagcttagtt aatcatgtta acaacaatt ctttgtaata     660
```

| | |
|---|---|
| ataaaattgt ctttcaacta gtccaagttt atgagttgat tcttcggaat aaattagaaa | 720 |
| atatcttaga ttttatactt cattgattat ttcatagagc aagtaggaga aataaaaata | 780 |
| tactagtatt atttactaaa aaaaatctaa gccacgtcgg aggataacat ccaacccagc | 840 |
| caatcacagc aatgttcatc agataaccca ctttaagccc acgcactctg agatccaaaa | 900 |
| atggttgagc tgttttggat ttggcaatta attgcatcgt ggcaacgtgg aattaacaaa | 960 |
| aatggagctg gaaatggtaa ttttcaaaaa tattttgtaa acgttttata ataatagaat | 1020 |
| tatttttca ctctctcatc gtcattatcg tcatcatcac tctctctctc tacgcttgca | 1080 |
| tatatataaa ccattgcaga gccgcggagt gtcaagcatc gtggtggagt agagtgagag | 1140 |
| aaccgaagcc aaaggcaact ccattattct ctctcgtgtt ctcgtgatat tggttttccg | 1200 |
| gcgccggagc ttgtcggtcc gtccgtccgt cc | 1232 |

```
<210> SEQ ID NO 5
<211> LENGTH: 1149
<212> TYPE: DNA
<213> ORGANISM: Artificial Sequence
<220> FEATURE:
<223> OTHER INFORMATION: AZprom_5 synthetic promoter

<400> SEQUENCE: 5
```

| | |
|---|---|
| gctgacaaga gagacggtgg tgaaaagaaa tctgcagctt ggatgccatt ggtgcacgca | 60 |
| gaggccttaa atgatgaga tgtacttgtg gctatggtta gggctaaggc tcgtgactgg | 120 |
| accagctttt gtaagacaag tcgaaagaga ccgctggctt aaaatgtgta ggccacgctc | 180 |
| acgggatggt ttaccagttc atttggtcgc atcctcttgc aagttttccc aacgtacatc | 240 |
| acactgggcg cttgcccaac aaattcgatg ctgacaagag agacggtggt gaaaagaaat | 300 |
| ctgcagcttg gatgccattg gtgcacgcag aggccttaaa tggatgagat gtacttgtgg | 360 |
| ctatggttag ggctaaggct cgtgactgga ccagcttttg taagacaagt cgaaagagac | 420 |
| cgctggctta aaatgtgtag gccacgctca cgggatggtt taccagttca tttggtcgca | 480 |
| tcctcttgca agttttccca acgtacatca cactgggcgc ttgcccaaca aattcgatgc | 540 |
| tgacaagaga gacggtggtg aaaagaaatc tgcagcttgg atgccattgg tgcacgcaga | 600 |
| ggccttaaat ggatgagatg tacttgtggc tatggttagg gctaaggctc gtgactggac | 660 |
| cagcttttgt aagacaagtc gaaagagacc gctggcttaa aatgtgtagg ccacgctcac | 720 |
| gggatggttt accagttcat ttggtcgcat cctcttgcaa gttttcccaa cgtacatcac | 780 |
| actgggcgct tgcccaacaa attcgataga tccaaaaatg gttgagctgt tttggatttg | 840 |
| gcaattaatt gcatcgtggc aacgtggaat taacaaaaat ggagctggaa atggtaattt | 900 |
| tcaaaaatat tttgtaaacg ttttataata atagaattat tttttcactc tctcatcgtc | 960 |
| attatcgtca tcatcactct ctctctctac gcttgcatat atataaacca ttgcagagcc | 1020 |
| gcggagtgtc aagcatcgtg gtggagtaga gtgagagaac cgaagccaaa ggcaactcca | 1080 |
| ttattctctc tcgtgttctc gtgatattgg ttttccggcg ccggagcttg tcggtccgtc | 1140 |
| cgtccgtcc | 1149 |

```
<210> SEQ ID NO 6
<211> LENGTH: 867
<212> TYPE: DNA
<213> ORGANISM: Artificial Sequence
<220> FEATURE:
<223> OTHER INFORMATION: AZprom_6 synthetic promoter

<400> SEQUENCE: 6
```

```
gatcgggtca gttttttgacg gctctacttc aaccccctccc atttcaaagt tccacatcat      60
ccgatataat ccgagcacaa ccaatgaaaa actagataat acccctttatt ggcccacaca     120 tcacaaaaat cctttaatcc aatgccacta aaaatcccac aaatgaaaac cacacaaaac     180
cgatcgggtc agtttttgac ggctctactt caaccccctcc catttcaaag ttccacatca    240
tccgatataa tccgagcaca accaatgaaa aactagataa taccctttat tggcccacac    300
atcacaaaaa tcctttaatc caatgccact aaaaatccca caaatgaaaa ccacacaaaa    360
ccgatcgggt cagttttttga cggctctact tcaaccccctc ccatttcaaa gttccacatc    420
atccgatata atccgagcac aaccaatgaa aaactagata tacccctta ttggcccaca     480 catcacaaaa atcctttaat ccaatgccac taaaaatccc acaaatgaaa accacacaaa     540
accgatcggg tcagtttttg acggctctac ttcaaccccct cccatttcaa agttccacat    600
catccgatat aatccgagca caaccaatga aaaactagat aatacccttt attggcccac    660
acatcacaaa aatcctttaa tccaatgcca ctaaaaatcc cacaaatgaa aaccacacaa    720
aaccatgtaa acagacatca cctcatctat cctccattttt atcacctctt attaaatccc    780
atcctcgctc tcagcactct ttggcaattg tcatttctta attgcattcc acttaaaccc    840
ctccaaaatc ctcctccttc caataca                                         867

<210> SEQ ID NO 7
<211> LENGTH: 1066
<212> TYPE: DNA
<213> ORGANISM: Artificial Sequence
<220> FEATURE:
<223> OTHER INFORMATION: AZprom_7 synthetic promoter

<400> SEQUENCE: 7
gatcgggtca gttttttgacg gctctacttc aaccccctccc atttcaaagt tccacatcat      60
ccgatataat ccgagcacaa ccaatgaaaa actagataat acccctttatt ggcccacaca     120 tcacaaaaat cctttaatcc aatgccacta aaaatcccac aaatgaaaac cacacaaaac     180
cgatcgggtc agtttttgac ggctctactt caaccccctcc catttcaaag ttccacatca    240
tccgatataa tccgagcaca accaatgaaa aactagataa taccctttat tggcccacac    300
atcacaaaaa tcctttaatc caatgccact aaaaatccca caaatgaaaa ccacacaaaa    360
ccgatcgggt cagttttttga cggctctact tcaaccccctc ccatttcaaa gttccacatc    420
atccgatata atccgagcac aaccaatgaa aaactagata tacccctta ttggcccaca     480 catcacaaaa atcctttaat ccaatgccac taaaaatccc acaaatgaaa accacacaaa     540
accgatcggg tcagtttttg acggctctac ttcaaccccct cccatttcaa agttccacat    600
catccgatat aatccgagca caaccaatga aaaactagat aatacccttt attggcccac    660
acatcacaaa aatcctttaa tccaatgcca ctaaaaatcc cacaaatgaa aaccacacaa    720
aaccagatcc aaaatggtt gagctgtttt ggatttggca attaattgca tcgtggcaac     780
gtggaattaa caaaaatgga gctggaaatg gtaatttttca aaaatatttt gtaaacgttt    840
tataataata gaattatttt ttcactctct catcgtcatt atcgtcatca tcactctctc    900
tctctacgct tgcatatata taaaccattg cagagccgcg gagtgtcaag catcgtggtg    960
gagtagagtg agagaaccga agccaaaggc aactccatta ttctctctcg tgttctcgtg    1020
atattggttt tccggcgccg gagcttgtcg gtccgtccgt ccgtcc                   1066

<210> SEQ ID NO 8
```

```
<211> LENGTH: 1405
<212> TYPE: DNA
<213> ORGANISM: Artificial Sequence
<220> FEATURE:
<223> OTHER INFORMATION: AZprom_8 synthetic promoter

<400> SEQUENCE: 8
tgagactttt caacaaaggg taatatcggg aaacctcctc ggattccatt gcccagctat    60
ctgtcacttc atcaaaagga cagtagaaaa ggaaggtggc acctacaaat gccatcattg   120
cgataaagga aaggctatcg ttcaagatgc ctctgccgac agtggtccca agatggacc    180 cccacccacg aggagcatcg tggaaaaaga agacgttcca accacgtctt caaagcaagt   240
ggattgatgt gatttaaaag taaaattcag acctcaataa ttccatcact taaactcata   300
agtaggcaca ggaggagcat caaagctctc caaaatgtga gttctgctct ctgaatgatg   360
atcctctgtt tctttcttct tcttaaacaa actcccaaac caagataccg aaccagaaga   420
agaagaagaa gtctccggta ccggtacgga ctgaccagat atctgaccca taccatatgg   480
taaagaagta gctgcatgat cctccatgaa ctgctcgtta tgcgcagtac tctgaacttt   540
gtttaacatg ataccaactc cttctatcat agccaacaac acacctccga ctaaagccga   600
tctagcagac gcgcctaagc cttgacgcaa cgagaggaat cctccagtgg ctgcaccaga   660
taagatcgag ttccatccat cttccttttg tcttgcgtac accaacgcac aatcgaaggt   720
tgagtaaaga ccaccccaca cggagaagct tcctccgctt tcggcccgc tcattctcaa    780 agcttgaacg ccgccggaga dacgagctcc gccgggagag ttgtagattc ctcttatgag   840
gtgatacgct gatccaccaa cagcacccat cgcaaacgca cctccgacat catctaggat   900
ccgatccgga catggctctc tcgatgattc tggagttccc attgatttc gattttgatc   960 tacaagtaac tttttagggt ataagaaaag agcccttgaa aacgaaacta agaatgagga  1020
aaaattacaa aaatggaaaa atatcgtgtt gttcacgtta cttgaccctg gtcaaagccc  1080
attaaggccc atttgtaaac acgctttatc acaaaatact aatataaaaa cgccacgtca  1140
ttcaagaacc ttatctttat ttaaaacgtg dacaaacatc ctccacctca taatgccatg  1200
tcacgacaca gtatctaaaa tcaaccaatc acaacgcgtc tttatagata acttgttttt  1260
ttatggagtt tgcttttaga gccatccatt gtcctatctc actttctctc tttcaccaca  1320
taaaaactca taaactcgat cgaaccaaag ctaaacgaaa aacttaaaac ccaaatctta  1380
tcactactct aaaagaatct tcatc                                        1405

<210> SEQ ID NO 9
<211> LENGTH: 1424
<212> TYPE: DNA
<213> ORGANISM: Artificial Sequence
<220> FEATURE:
<223> OTHER INFORMATION: AZprom_9 synthetic promoter

<400> SEQUENCE: 9
caatccgtca tattttttca accttaaaaa tatttattat gggtaaaaat accttaatat    60 ttttttata aaacaattt tttatttaaa tacatatgta aataataaaa atattaaaaa    120
atatttatat aaaaaatgag ttattcttca aattcaaaaa taaaaatat atctaaaatg   180 caagtttgac ctaataaatg caacgtcatc attttttaaa atatttttta cagaatcaaa   240
ttaaaagaat tcttattttt tctcatttta gaacaagata acaataataa tcttatttta   300
aaaaatactt catatattaa aaattactat atatataccc catttgata ttttttatca    360 tttatattga caaaaaatat ttaaaaaata ttttatttat tcgtattttt aataacattt   420
```

```
ttaatcaaat aaaagtagac agcgtagcat aacatgaaat cttgaaaaca ttgcgtgaga      480
aggaagaatt aggataagga actgggaaag agtccaaatg tcaaaagcac atctaaaaac      540
attaaagcta aagattctgt aacttttta tcattatttt tgttcgattc tatcttctac       600
cattttgttg ataacattta cttaaaagaa tcataaagca aggtgcctta aaaatcaatc      660
acataatcga aacattcagg cattttgttg tttatgaact tgaataaatg ttcccattaa      720
tcatggatca aatgtgtcac catgcaaatg tgtgatcttg aaattctgcc acgaaaagag      780
gataaagtga taaggaatat ggccagatca gcttcatttt taaggtaatg gcgatcttta      840
gacaggacgt ggcatctctt ttaattttg gtcggatatg tatggtaagt gataatatat       900
atattttgat attattcttt gagaatgttg ttaccaactt accgaagatc acccaccgtg      960
tcatgtgtgt agctctgcct cccataatta tgtaatcaaa agaggccacg tcaacaaatg     1020
atttgactaa caaccgaaga tttaaagaa aggaataaat tcgtaaatta aggggtgttt      1080
gtgcaaatag atccaaaaat ggttgagctg ttttggatt ggcaattaat tgcatcgtgg      1140
caacgtggaa ttaacaaaaa tggagctgga aatggtaatt ttcaaaaata ttttgtaaac     1200
gttttataat aatagaatta ttttttcact ctctcatcgt cattatcgtc atcatcactc     1260
tctctctcta cgtctccact gacgtaaggg atgacgcaca atcccactat ccttcgcaag     1320
acccttcctc tatataagga agttcatttc atttggagag acacgctga ggaactaatt      1380 cactcattgg attcatagaa gtccattcct cctaagtatc taaa                      1424

<210> SEQ ID NO 10
<211> LENGTH: 1004
<212> TYPE: DNA
<213> ORGANISM: Artificial Sequence
<220> FEATURE:
<223> OTHER INFORMATION: AZprom_10 synthetic promoter

<400> SEQUENCE: 10
gatcgggtca gttttttgacg gctctacttc aaccctccc atttcaaagt tccacatcat        60
ccgatataat ccgagcacaa ccaatgaaaa actagataat acccttatt ggcccacaca        120 tcacaaaaat cctttaatcc aatgccacta aaaatcccac aaatgaaaac cacacaaaac       180
cgatcgggtc agttttgac ggctctactt caaccctcc catttcaaag ttccacatca        240
tccgatataa tccgagcaca accaatgaaa aactagataa tacccttat tggcccacac        300 atcacaaaaa tcctttaatc caatgccact aaaaatccca caatgaaaa ccacacaaaa       360 ccgataagga atatggccag atcagcttca tttttaaggt aatggcgatc tttagacagg       420
acgtggcatc tcttttaatt tttggtcgga tatgtatggt aagtgataat atatatattt       480
tgatattatt ctttgagaat gttgttacca acttaccgaa gatcacccac cgtgtcatgt       540
gtgtagctct gcctcccata attatgtaat caaagaggc cacgtcaaca atgatttga       600 ctaacaaccg aagatttaaa agaaggaat aaattcgtaa attaagggt gtttgtgcaa        660 atagatccaa aaatggttga gctgttttgg atttggcaat taattgcatc gtggcaacgt       720
ggaattaaca aaatggagc tggaaatggt aattttcaaa atattttgt aaacgtttta       780 taataataga attattttt cactctctca tcgtcattat cgtcatcatc actctctctc       840
tctacgcttg catatatata aaccattgca gagccgcgga gtgtcaagca tcgtggtgga      900
gtagagtgag agaaccgaag ccaaaggcaa ctccattatt ctctctcgtg ttctcgtgat      960
attggttttc cggcgccgga gcttgtcggt ccgtccgtcc gtcc                       1004
```

<210> SEQ ID NO 11
<211> LENGTH: 895
<212> TYPE: DNA
<213> ORGANISM: Artificial Sequence
<220> FEATURE:
<223> OTHER INFORMATION: AZprom_11 synthetic promoter

<400> SEQUENCE: 11

```
tgagactttt caacaaaggg taatatcggg aaacctcctc ggattccatt gcccagctat      60
ctgtcacttc atcaaaagga cagtagaaaa ggaaggtggc acctacaaat gccatcattg     120
cgataaagga aaggctatcg ttcaagatgc ctctgccgac agtggtccca agatggacc     180
cccacccacg aggagcatcg tggaaaaaga agacgttcca accacgtctt caaagcaagt     240
ggattgatgt gatgataagg aatatggcca gatcagcttc attttttaagg taatggcgat     300
ctttagacag gacgtggcat ctcttttaat ttttggtcgg atatgtatgg taagtgataa     360
tatatatatt ttgatattat tctttgagaa tgttgttacc aacttaccga agatcaccca     420
ccgtgtcatg tgtgtagctc tgcctcccat aattatgtaa tcaaaagagg ccacgtcaac     480
aaatgatttg actaacaacc gaagatttaa agaaaggaa taaattcgta aattaagggg     540
tgtttgtgca aatagatcca aaaatggttg agctgttttg gatttggcaa ttaattgcat     600
cgtggcaacg tggaattaac aaaaatggag ctggaaatgg taattttcaa aaatattttg     660
taaacgtttt ataataatag aattatttt tcactctctc atcgtcatta tcgtcatcat     720
cactctctct ctctacgctt gcatatatat aaaccattgc agagccgcgg agtgtcaagc     780
atcgtggtgg agtagagtga gagaaccgaa gccaaaggca actccattat tctctctcgt     840
gttctcgtga tattggtttt ccggcgccgg agcttgtcgg tccgtccgtc cgtcc          895
```

<210> SEQ ID NO 12
<211> LENGTH: 1415
<212> TYPE: DNA
<213> ORGANISM: Artificial Sequence
<220> FEATURE:
<223> OTHER INFORMATION: AZprom_12 synthetic promoter

<400> SEQUENCE: 12

```
caatccgtca tatttttca accttaaaaa tatttattat gggtaaaaat accttaatat      60
tttttttata aaacaattt tttatttaaa tacatatgta aataataaaa atattaaaaa     120
atatttatat aaaaaatgag ttattcttca aattcaaaaa taaaaaatat atctaaaatg     180
caagtttgac ctaataaatg caacgtcatc attttttaaa atattttta cagaatcaaa     240
ttaaaagaat tcttattttt tctcatttta gaacaagata acaataataa tcttatttta     300
aaaaatactt catatattaa aaattactat atatataccc catttttgata tttttttatca     360
tttatattga caaaaaatat ttaaaaaata ttttatttat tcgtattttt aataacattt     420
ttaatcaaat aaaagtagac agcgtagcat aacatgaaat cttgaaaaca ttgcgtgaga     480
aggaagaatt aggataagga actgggaaag agtccaaatg tcaaaagcac atctaaaaac     540
attaaagcta agattctgt aactttttta tcattatttt tgttcgattc tatcttctac     600
cattttgttg ataacattta cttaaaagaa tcataaagca aggtgcctta aaaatcaatc     660
acataatcga acattcagg cattttgttg tttatgaact tgaataaatg ttcccattaa     720
tcatggatca aatgtgtcac catgcaaatg tgtgatcttg aaattctgcc acgaaaagag     780
gataaagtga taaggaatat ggccagatca gcttcatttt taaggtaatg gcgatcttta     840
gacaggacgt ggcatctctt taattttttg gtcggatatg tatggtaagt gataatatat     900
```

```
atattttgat attattcttt gagaatgttg ttaccaactt accgaagatc acccaccgtg    960
tcatgtgtgt agctctgcct cccataatta tgtaatcaaa agaggccacg tcaacaaatg   1020
atttgactaa caaccgaaga tttaaaagaa aggaataaat tcgtaaatta agggtgtttt   1080
gtgcaaatag atccaaaaat ggttgagctg ttttggattt ggcaattaat tgcatcgtgg   1140
caacgtggaa ttaacaaaaa tggagctgga aatggtaatt ttcaaaaata ttttgtaaac   1200
gttttataat aatagaatta ttttttcact ctctcatcgt cattatcgtc atcatcactc   1260
tctctctcta cgatgtaaac agacatcacc tcatctatcc tccattttat cacctcttat   1320
taaatcccat cctcgctctc agcactcttt ggcaattgtc atttcttaat tgcattccac   1380
ttaaacccct ccaaaatcct cctccttcca ataca                              1415

<210> SEQ ID NO 13
<211> LENGTH: 848
<212> TYPE: DNA
<213> ORGANISM: Artificial Sequence
<220> FEATURE:
<223> OTHER INFORMATION: AZprom_13 synthetic promoter

<400> SEQUENCE: 13
tgagactttt caacaaaggg taatatcggg aaacctcctc ggattccatt gcccagctat     60
ctgtcacttc atcaaaagga cagtagaaaa ggaaggtggc acctacaaat gccatcattg    120
cgataaagga aaggctatcg ttcaagatgc ctctgccgac agtggtccca agatggacc     180 cccacccacg aggagcatcg tggaaaaaga agacgttcca accacgtctt caaagcaagt    240
ggattgatgt gattgagact tttcaacaaa gggtaatatc gggaaacctc ctcggattcc    300
attgcccagc tatctgtcac ttcatcaaaa ggacagtaga aaggaaggt ggcacctaca    360 aatgccatca ttgcgataaa ggaaaggcta tcgttcaaga tgcctctgcc gacagtggtc    420
ccaaagatgg accccacccc acgaggagca tcgtggaaaa agaagacgtt ccaaccacgt    480
cttcaaagca agtggattga tgtgatagat ccaaaaatgg ttgagctgtt ttggatttgg    540
caattaattg catcgtggca acgtggaatt aacaaaaatg gagctggaaa tggtaatttt    600
caaaaatatt ttgtaaacgt tttataataa tagaattatt ttttcactct ctcatcgtca    660
ttatcgtcat catcactctc tctctctacg cttgcatata tataaaccat tgcagagccg    720
cggagtgtca agcatcgtgg tggagtagag tgagagaacc gaagcaaag gcaactccat    780 tattctctct cgtgttctcg tgatattggt tttccggcgc cggagcttgt cggtccgtcc    840
gtccgtcc                                                            848

<210> SEQ ID NO 14
<211> LENGTH: 1148
<212> TYPE: DNA
<213> ORGANISM: Artificial Sequence
<220> FEATURE:
<223> OTHER INFORMATION: AZprom_14 synthetic promoter

<400> SEQUENCE: 14
tgagactttt caacaaaggg taatatcggg aaacctcctc ggattccatt gcccagctat     60
ctgtcacttc atcaaaagga cagtagaaaa ggaaggtggc acctacaaat gccatcattg    120
cgataaagga aaggctatcg ttcaagatgc ctctgccgac agtggtccca agatggacc     180 cccacccacg aggagcatcg tggaaaaaga agacgttcca accacgtctt caaagcaagt    240
ggattgatgt gattgagact tttcaacaaa gggtaatatc gggaaacctc ctcggattcc    300
```

```
attgcccagc tatctgtcac ttcatcaaaa ggacagtaga aaaggaaggt ggcacctaca      360
aatgccatca ttgcgataaa ggaaaggcta tcgttcaaga tgcctctgcc gacagtggtc      420
ccaaagatgg accccaccc acgaggagca tcgtggaaaa agaagacgtt ccaaccacgt       480
cttcaaagca agtggattga tgtgatgata aggaatatgg ccagatcagc ttcattttta      540
aggtaatggc gatctttaga caggacgtgg catctctttt aattttggt cggatatgta       600 tggtaagtga taatatatat attttgatat tattctttga aatgttgtt accaacttac       660 cgaagatcac ccaccgtgtc atgtgtgtag ctctgcctcc cataattatg taatcaaaag      720
aggccacgtc aacaaatgat ttgactaaca accgaagatt taaagaaag gaataaattc       780 gtaaattaag gggtgtttgt gcaaatagat ccaaaaatgg ttgagctgtt ttggatttgg      840
caattaattg catcgtggca acgtggaatt aacaaaaatg gagctggaaa tggtaatttt      900
caaaaatatt ttgtaaacgt tttataataa tagaattatt ttttcactct ctcatcgtca      960
ttatcgtcat catcactctc tctctctacg cttgcatata tataaaccat tgcagagccg     1020
cggagtgtca agcatcgtgg tggagtagag tgagagaacc gaagccaaag gcaactccat     1080
tattctctct cgtgttctcg tgatattggt tttccggcgc cggagcttgt cggtccgtcc     1140
gtccgtcc                                                             1148

<210> SEQ ID NO 15
<211> LENGTH: 1049
<212> TYPE: DNA
<213> ORGANISM: Artificial Sequence
<220> FEATURE:
<223> OTHER INFORMATION: AZprom_15 synthetic promoter

<400> SEQUENCE: 15
tgagactttt caacaaaggg taatatcggg aaacctcctc ggattccatt gcccagctat       60
ctgtcacttc atcaaaagga cagtagaaaa ggaaggtggc acctacaaat gccatcattg      120
cgataaagga aaggctatcg ttcaagatgc ctctgccgac agtggtccca agatggacc       180 cccacccacg aggagcatcg tggaaaaaga agacgttcca accacgtctt caaagcaagt      240
ggattgatgt gatgatttcc attgacggag ggcaaaatcg ttggtgagac cgagctccaa      300
aagaccggtt ccgtcatcaa gtaccagaca attatcgccg cctccaccgg agaaggggac      360
caaaacgccc tgcaacgcaa gacttgaagt catcgaaaca ggaattaaca atttagctat      420
agacaatgag aggatgatag attgggaacc tgtaaccaag cacgttgaaa agtacaccg      480 cctagggagg cggcgttctg agaaggcgtc ggtttagcgt cccggagctg agaacaaagc      540
atcttcaccg ccgctaagct gtagtccatt ttacccgccg atccgactcg gctgatcaat      600
ttcacaaatg cctttacctc atcgattacc ggattaaacc gaaccgaaca aatggtatcg      660
gtacagtaat ttgattttga ttttggcag atattgggag agggaatatt gtgtttgaaa      720 aaaaaaaat ggaattcatg gtgttttggc tttttgacta attaaaatca ttaacatgca      780
aactaaaaga tgtaaaaatc tttataaaat acaaacaaa aaaataaaca aatttgaga       840 caaaaataa atctggaatc aatcttatcc aagaaataga cccacaatat caagaaaat       900 aatgaggtgt cacaaagcta ttgattgata acacatcctc gaaatctctc tctttgtcca      960
cagaataaaa atctatttct tgtgttgtg ttgtatttac ttaaaaaaat aaaggagatc     1020
agtttgggag aaagcagcaa agaagaaaa                                      1049

<210> SEQ ID NO 16
<211> LENGTH: 977
```

```
<212> TYPE: DNA
<213> ORGANISM: Artificial Sequence
<220> FEATURE:
<223> OTHER INFORMATION: AZprom_16 synthetic promoter

<400> SEQUENCE: 16
gatcgggtca gttttgacg gctctacttc aaccctccc atttcaaagt tccacatcat      60
ccgatataat ccgagcacaa ccaatgaaaa actagataat acccttttatt ggcccacaca    120
tcacaaaaat cctttaatcc aatgccacta aaatcccac aaatgaaaac cacacaaaac    180
cgatttccat tgacggaggg caaaatcgtt ggtgagaccg agctccaaaa gaccggttcc    240
gtcatcaagt accagacaat tatcgccgcc tccaccggag aagggacca aaacgccctg    300
caacgcaaga cttgaagtca tcgaaacagg aattaacaat ttagctatag acaatgagag    360
gatgatagat tgggaacctg taaccaagca cgttgaaaaa gtacaccgcc tagggaggcg    420
gcgttctgag aaggcgtcgg tttagcgtcc cggagctgag aacaaagcat cttcaccgcc    480
gctaagctgt agtccatttt acccgccgat ccgactcggc tgatcaattt cacaaatgcc    540
tttacctcat cgattaccgg attaaaccga accgaacaaa tggtatcggt acagtaattt    600
gattttgatt tttggcagat attgggagag ggaatattgt gtttgaaaaa aaaaaaatgg    660
aattcatggt gttttggctt tttgactaat taaaatcatt aacatgcaaa ctaaaagatg    720
taaaaatctt tataaaatac aaacaaaaaa aataaacaaa ttttgagaca aaaaataaat    780
ctggaatcaa tcttatccaa gaaatagacc cacaatatca aagaaaataa tgaggtgtca    840
caaagctatt gattgataac acatcctcga aatctctctc tttgtccaca gaataaaaat    900
ctatttcttg tgtttgtgtt gtatttactt aaaaaaaataa aggagatcag tttgggagaa    960
agcagcaaag aagaaaa                                                    977

<210> SEQ ID NO 17
<211> LENGTH: 743
<212> TYPE: DNA
<213> ORGANISM: Artificial Sequence
<220> FEATURE:
<223> OTHER INFORMATION: AZprom_17 synthetic promoter

<400> SEQUENCE: 17
tgagactttt caacaaaggg taatatcggg aaacctcctc ggattccatt gcccagctat      60
ctgtcacttc atcaaaagga cagtagaaaa ggaaggtggc acctacaaat gccatcattg    120
cgataaagga aaggctatcg ttcaagatgc ctctgccgac agtggtccca aagatggacc    180
cccacccacg aggagcatcg tggaaaaaga agacgttcca accacgtctt caaagcaagt    240
ggattgatgt gatggcttat gaatctgacg tggaacaaga agaaagcgta tctgccacgt    300
ggcacaatac aacacctcaa cagccttatc tggacatcaa cagagagatc ctccaatatc    360
cgaaaccaac caatcagctt cactcttggt ttcacctcca tacattaaca caccaacaag    420
gcttatgaat ctgacgtgga acaagaagaa agcgtatctg ccacgtggca aatacaaca    480
cctcaacagc cttatctgga catcaacaga gagatcctcc aatatccgaa accaaccaat    540
cagcttcact cttggtttca cctccataca ttaacacacc aacaatctcc actgacgtaa    600
gggatgacgc acaatcccac tatccttcgc aagacccttc ctctatataa ggaagttcat    660
ttcatttgga gaggacacgc tgcatattgg aagttaaagg aaaagagaga aagagaaatc    720
tttctgtcta agtgtaatta aca                                            743

<210> SEQ ID NO 18
```

<211> LENGTH: 794
<212> TYPE: DNA
<213> ORGANISM: Artificial Sequence
<220> FEATURE:
<223> OTHER INFORMATION: AZprom_18 synthetic promoter

<400> SEQUENCE: 18

```
gctggtggac tagagattgc cacgtaagac tactaaacga taaaacaaaa atcttaaaat      60
ccaatgaatg aacagataaa gattacttca gatataacaa acgttacaat atcccgctgg     120
tggactagag attgccacgt aagactacta acgataaaaa caaaaatctt aaaatccaat     180
gaatgaacag ataaagatta cttcagatat aacaaacgtt acaatatccc gtaaaacgtc     240
aaagttttaa ggtgatatca cataattcat gagattattt tggttattgg ataaagtgac     300
gatgaaatcg attcataatt gaaattaaac tggtagtgat gatgaactaa ttaccattga     360
aaatattgat atttatgtgt gggtaaatgc tttttataat gttactttat attaatgttt     420
cgatcatcag aatctatatt ttcaaaatgt tatactttaa gttttagtta ttgggttgta     480
gcaaaaatca ttcttgtcac gagggtgtaa gtaagtgtaa ccgttgaagt attcagtggc     540
tcataacttg tggtcacaaa acgcttggct gcaatgaaaa aatcaaaaca aatgctggtg     600
gactagagat tgccacgtaa gactactaaa cgataaaaca aaaatcttaa aatccaatga     660
atgaacagat aaagattact tcagatataa caaacgttac aatatcccta tataatccaa     720
cactatcgaa ccagttttaa tcactctcac tcacaagtta gtcataaaaa aaaaaaaac     780
acaaaaaagt ttca                                                        794
```

<210> SEQ ID NO 19
<211> LENGTH: 863
<212> TYPE: DNA
<213> ORGANISM: Artificial Sequence
<220> FEATURE:
<223> OTHER INFORMATION: AZprom_19 synthetic promoter

<400> SEQUENCE: 19

```
caatccgtca tatttttca acctaaatgc aacgtcatca aaagtagac agcgtagcat      60
aacatgaaat cttgaaaaca ttgcgtgaga aggaagaatt aggataagga actgggaaag     120
tgttgtttat gaacttgaat aaatgttccc attaatcatg gatcaaatgt gtcaccatgc     180
aaatgtgtga tcttgaaatt ctgccacgaa aagcttagaa caggacgtgg catgccacgt     240
caacaaacaa atagatccaa aaatggttga gctgttttgg atttggcaat taattgcatc     300
gtggcaaatt ttttcactct ctcatcgtca ttatcgtcat catcactctc tctctctacg     360
cttgcacaat ccgtcatatt tttcaacct aaatgcaacg tcatcaaaaa gtagacagcg     420
tagcataaca tgaaatcttg aaaacattgc gtgagaagga agaattagga taaggaactg     480
ggaaagtgtt gtttatgaac ttgaataaat gttcccatta atcatggatc aaatgtgtca     540
ccatgcaaat gtgtgatctt gaaattctgc cacgaaaagc tttagacagg acgtggcatg     600
ccacgtcaac aaacaaatag atccaaaaat ggttgagctg ttttggattt ggcaattaat     660
tgcatcgtgg caattttttt cactctctca tcgtcattat cgtcatcatc actctctctc     720
tctacgcttg cagtccgtca gatataggaa atatgtaaaa ccttatcatt atatataggg     780
tggtgggcaa ctatgcaatg accatattgg aagttaaagg aaaagagaga aagagaaatc     840
tttctgtcta agtgtaatta aca                                              863
```

<210> SEQ ID NO 20
<211> LENGTH: 934

```
<212> TYPE: DNA
<213> ORGANISM: Artificial Sequence
<220> FEATURE:
<223> OTHER INFORMATION: AZprom_20 synthetic promoter

<400> SEQUENCE: 20
aaaggaaata gtggtgttgc atcaagttat ggacaatata aggaagcaaa cagtactcta      60
gctatcaaat tagtttccac ttctaaacca taaagccaag gaaaagggac tctaaaaaaa     120
ttaaccaacg ataagattac taggtcttac acgtggcacc tccattgtgg tgactaaatg     180
aagagtggct tagctcaaaa tataattttc caacctttca tgtgtggata ttaagttttg     240
tgtagtgaat caagaaccac ataatccaat ggttagcttt attccaagat gaggggttg      300 ttgattttg tccgtcagat ataggaaata tgtaaaacct tatcataaag gaaatagtgg      360
tgttgcatca agttatggac aatataagga agcaaacagt actctagcta tcaaattagt     420
ttccacttct aaaccataaa gccaaggaaa agggactcta aaaaattaa ccaacgataa       480 gattactagg tcttacacgt ggcacctcca ttgtggtgac taaatgaaga gtggcttagc     540
tcaaaatata attttccaac ctttcatgtg tggatattaa gttttgtgta gtgaatcaag     600
aaccacataa tccaatggtt agctttattc caagatgagg gggttgttga ttttgtccg       660 tcagatatag gaaatatgta aaaccttatc attatttgt aaacgtttta taataataga     720 attattttt cactctctca tcgtcattat cgtcatcatc actctctctc tctacgcttg      780
catatatata aaccattgca gagccgcgga gtgtcaagca tcgtggtgga gtagagtgag     840
agaaccgaag ccaaaggcaa ctccattatt ctctctcgtg ttctcgtgat attggttttc     900
cggcgccgga gcttgtcggt ccgtccgtcc gtcc                                 934

<210> SEQ ID NO 21
<211> LENGTH: 1400
<212> TYPE: DNA
<213> ORGANISM: Artificial Sequence
<220> FEATURE:
<223> OTHER INFORMATION: AZprom_21 synthetic promoter

<400> SEQUENCE: 21
tgagactttt caacaaaggg taatatcggg aaacctcctc ggattccatt gcccagctat      60
ctgtcacttc atcaaaagga cagtagaaaa ggaaggtggc acctacaaat gccatcattg     120
cgataaagga aaggctatcg ttcaagatgc ctctgccgac agtggtccca agatggacc      180 cccacccacg aggagcatcg tggaaaaaga agacgttcca accacgtctt caaagcaagt     240
ggattgatgt gattacatac tttccaaatt catagaaaat cttcaatgtt gtattagatt     300
atgtctttaa cacacaaaat tgacgcatta acgcctctat gtagagaata ttattgtact     360
taatttccat ttctcaatat atatgcaaca tattcacaca cacacacaca tatatatata     420
catatataca tacatacata tatatatata tatatatata tgtgtgtgtg tgtgtgtata     480
tatatatata catatatata tatatataca tacatatata tatatatata tatatatata     540
tatatgtatc atgacaaaaa gaaaatgttc gattcatctt tttatggagg attttgtttg     600
tttcagtttt ttgtttgttt tagttttttg tttgttttag tgagtaagta cagctctcat     660
aaattcacat gatttcaacc atagaaatat agtctcaata ttgtccacgt ataagctcat     720
tatcctttcc gtggatttgt tttgttttc tattgtgtaa cgagaaatat tcgaataaaa     780
acatagatgc aatactcctg tcctggtgag tccttttttc atgttctaga cggtgttaat     840
gatggatgat gttaaatgac atcgttttaa tactaattgt tttttaattt acaaaactct     900
```

| caacaaatga ttagttgggt tagttattca taggaaagcg gacgagcatg tcgttataat | 960 |
| taaaaaaata tcaaaagagt aaacaaaaaa ggaaaaagac taattatta gataataata | 1020 |
| atatccacaa aaatattcga attcttcaat cctgagtttg ctctgtggat gagtttctgt | 1080 |
| atcattgata cttgatacct gtaattcaca cacctcatat ctcatacttc atctataaat | 1140 |
| acccaattca ttttgctcaa agtctcaaca ctgagcatac ccaatattca ggtgatctaa | 1200 |
| tttaacgttt gcatgagtat tttcttaata aaatttatgt tgggtttaca gtatctattg | 1260 |
| ggtggatttc ttaaacggat tgtggtttga ttaataaaaa atcttaatga aagtttgtg | 1320 |
| ataatatgct gaaatgggtt gttttttgtgt taattttttca gggttggagg ggaattaagt | 1380 |
| attaagcaag ggtgtgagta | 1400 |

<210> SEQ ID NO 22
<211> LENGTH: 351
<212> TYPE: DNA
<213> ORGANISM: Cauliflower mosaic virus

<400> SEQUENCE: 22

| tgagactttt caacaaaggg taatatcggg aaacctcctc ggattccatt gcccagctat | 60 |
| ctgtcacttc atcaaaagga cagtagaaaa ggaaggtggc acctacaaat gccatcattg | 120 |
| cgataaagga aaggctatcg ttcaagatgc ctctgccgac agtggtccca agatggacc | 180 |
| cccacccacg aggagcatcg tggaaaaaga agacgttcca accacgtctt caaagcaagt | 240 |
| ggattgatgt gatatctcca ctgacgtaag ggatgacgca caatcccact atccttcgca | 300 |
| agacccttcc tctatataag gaagttcatt tcatttggag aggactaaac c | 351 |

<210> SEQ ID NO 23
<211> LENGTH: 815
<212> TYPE: DNA
<213> ORGANISM: Cauliflower mosaic virus

<400> SEQUENCE: 23

| caacatggtg gagcacgaca ctctcgtcta ctccaagaat atcaaagata cagtctcaga | 60 |
| agaccaaagg gctattgaga cttttcaaca aagggtaata tcgggaaacc tcctcggatt | 120 |
| ccattgccca gctatctgtc acttcatcaa aaggacagta gaaaaggaag gtggcaccta | 180 |
| caaatgccat cattgcgata aaggaaaggc tatcgttcaa gatgcctctg ccgacagtgg | 240 |
| tcccaaagat ggacccccac ccacgaggag catcgtggaa aagaagacg ttccaaccac | 300 |
| gtcttcaaag caagtggatt gatgtgataa catggtggag cacgacactc tcgtctactc | 360 |
| caagaatatc aaagatacag tctcagaaga ccaaagggct attgagactt tcaacaaag | 420 |
| ggtaatatcg ggaaacctcc tcggattcca ttgcccagct atctgtcact tcatcaaaag | 480 |
| gacagtagaa aaggaaggtg gcacctacaa atgccatcat tgcgataaag gaaaggctat | 540 |
| cgttcaagat gcctctgccg acagtggtcc caaagatgga ccccccaccca cgaggagcat | 600 |
| cgtggaaaaa gaagacgttc caaccacgtc ttcaaagcaa gtggattgat gtgatatctc | 660 |
| cactgacgta agggatgacg cacaatccca ctatccttcg caagaccttc ctctatataa | 720 |
| ggaagttcat ttcatttgga gaggacacgc tgaaatcacc agtctctctc tacaaatcta | 780 |
| tctctctcga gctttcgcag aactgtcgat cgacc | 815 |

<210> SEQ ID NO 24
<211> LENGTH: 366
<212> TYPE: DNA
<213> ORGANISM: Artificial Sequence
<220> FEATURE:
<223> OTHER INFORMATION: modified VPP promoter

<400> SEQUENCE: 24

| | | | | | |
|---|---|---|---|---|---|
| caatccgtca | tattttttca | acctaaatgc | aacgtcatca | aaaagtagac | agcgtagcat | 60 |
| aacatgaaat | cttgaaaaca | ttgcgtgaga | aggaagaatt | aggataagga | actgggaaag | 120 |
| tgttgtttat | gaacttgaat | aaatgttccc | attaatcatg | gatcaaatgt | gtcaccatgc | 180 |
| aaatgtgtga | tcttgaaatt | ctgccacgaa | aagctttaga | caggacgtgg | catgccacgt | 240 |
| caacaaacaa | atagatccaa | aaatggttga | gctgttttgg | atttggcaat | taattgcatc | 300 |
| gtggcaaatt | ttttcactct | ctcatcgtca | ttatcgtcat | catcactctc | tctctctacg | 360 |
| cttgca | | | | | | 366 |

<210> SEQ ID NO 25
<211> LENGTH: 346
<212> TYPE: DNA
<213> ORGANISM: Artificial Sequence
<220> FEATURE:
<223> OTHER INFORMATION: modified ribulose-1,5-bisphosphate carboxylase
    small subunit promoter (RBCss)

<400> SEQUENCE: 25

| | | | | | |
|---|---|---|---|---|---|
| aaaggaaata | gtggtgttgc | atcaagttat | ggacaatata | aggaagcaaa | cagtactcta | 60 |
| gctatcaaat | tagtttccac | ttctaaacca | taaagccaag | gaaaagggac | tctaaaaaaa | 120 |
| ttaaccaacg | ataagattac | taggtcttac | acgtggcacc | tccattgtgg | tgactaaatg | 180 |
| aagagtggct | tagctcaaaa | tataatttc | caacctttca | tgtgtggata | ttaagttttg | 240 |
| tgtagtgaat | caagaaccac | ataatccaat | ggttagcttt | attccaagat | gaggggttg | 300 |
| ttgattttg | tccgtcagat | ataggaaata | tgtaaaacct | tatcat | | 346 |

<210> SEQ ID NO 26
<211> LENGTH: 577
<212> TYPE: DNA
<213> ORGANISM: Artificial Sequence
<220> FEATURE:
<223> OTHER INFORMATION: inverted DR region of Ft-PEPc promoter

<400> SEQUENCE: 26

| | | | | | |
|---|---|---|---|---|---|
| tacatactt | ccaaattcat | agaaaatctt | caatgttgta | ttagattatg | tctttaacac | 60 |
| acaaaattga | cgcattaacg | cctctatgta | gagaatatta | ttgtacttaa | tttccatttc | 120 |
| tcaatatata | tgcaacatat | tcacacacac | acacacatat | atatatacat | atatacatac | 180 |
| atacatatat | atatatatat | atatatatgt | gtgtgtgtgt | gtgtatatat | atatatacat | 240 |
| atatatatat | atatacatat | acatatatat | atatatatat | atatatatat | atgtatcatg | 300 |
| acaaaaagaa | aatgttcgat | tcatcttttt | atggaggatt | ttgtttgttt | cagtttttg | 360 |
| tttgttttag | ttttttgttt | gttttagtga | gtaagtacag | ctctcataaa | ttcacatgat | 420 |
| ttcaaccata | gaaatatagt | ctcaatattg | tccacgtata | agctcattat | cctttccgtg | 480 |
| gatttgtttt | gttttctat | tgtgtaacga | gaaatattcg | aataaaaaca | tagatgcaat | 540 |
| actcctgtcc | tggtgagtcc | tttttcatg | ttctaga | | | 577 |

<210> SEQ ID NO 27
<211> LENGTH: 25
<212> TYPE: DNA
<213> ORGANISM: Artificial Sequence
<220> FEATURE:
<223> OTHER INFORMATION: YPet_frw primer

```
<220> FEATURE:
<221> NAME/KEY: primer
<222> LOCATION: (1)..(25)

<400> SEQUENCE: 27
ctcagtaagt ggggaaggtg aaggc                                          25

<210> SEQ ID NO 28
<211> LENGTH: 25
<212> TYPE: DNA
<213> ORGANISM: Artificial Sequence
<220> FEATURE:
<223> OTHER INFORMATION: YPet_rev primer
<220> FEATURE:
<221> NAME/KEY: primer
<222> LOCATION: (1)..(25)

<400> SEQUENCE: 28
tgccagctga acacctccat cctcg                                          25

<210> SEQ ID NO 29
<211> LENGTH: 237
<212> TYPE: DNA
<213> ORGANISM: Homo sapiens

<400> SEQUENCE: 29
ttccccattc ctctcccta ttgctggctc tgcagggctc tgatcaagcg atccaagcc      60 atgattccca agggtgcgct agctgtggca gtggcccagg tgtgccgcgt ggtacctctg   120
gtggcgggcg gcatctgcca gtgcctggct gagcgctact ccgtcatcct gctcgacacg   180
ctgctgggcc gcatgctgcc ccagctggtc tgccgcctcg tcctccggtg ctccatg     237

<210> SEQ ID NO 30
<211> LENGTH: 1827
<212> TYPE: DNA
<213> ORGANISM: Artificial Sequence
<220> FEATURE:
<223> OTHER INFORMATION: AZ18_1xSP-B (YPet - linker1 - TEV-1xSP-B -
      TEV - linker2 - YPet) construct

<400> SEQUENCE: 30
atggcttcta aaggagaaga attgtttact ggtgtagtgc ctatccttgt tgaattggat    60
ggtgatgtta atggccacaa attctcagta agtggggaag gtgaaggcga cgctacatat   120
ggaaagctca ctcttaagct gctatgtact actggaaagt gcccgtccc ttggccaaca   180 ttggttacaa cacttggata tgggttcag tgttttgcaa gatatccaga ccacatgaag   240
caacatgact tcttcaaatc tgctatgcca gagggatatg tccaagaaag gacaatattc   300
ttcaaggatg atggaaatta caagacaaga gctgaggtga agtttgaagg cgatacactg   360
gttaacagaa tcgaactaaa gggcattgat ttcaaggaag atggaaatat cttagggcat   420
aagctggagt ataactataa ctctcataat gtttacataa ccgcagacaa gcagaaaaac   480
gggattaagg caaatttcaa gattaggcat aacatcgagg atggaggtgt tcagctggca   540
gaccattatc agcaaaatac accaataggt gatggcccag tcttattgcc tgataaccat   600
tatctctcct atcagagtgc tctctttaag gaccctaacg aaaagagaga tcatatggtc   660
ttacttgagt tcttgactgc agccggaatt accgaaggga tgaacgaact ttacaaggag   720
cccgagccgg agcctgagcc agaaccagag ccagagccgc cgaaaatctt tactttcaa   780 ggtttcccta tcccactgcc ttactgctgg ctttgtcgag cccttatcaa gaggattcaa   840
gcaatgatcc caaaaggtgc cttagcagtc gccgtggccc aagtttgcag agtagtgcct   900
```

```
cttgttgctg gcggaatttg ccaatgtctt gcagagcgtt acagcgttat tctgttggat      960
actctgttgg gcagaatgct acctcaattg gtgtgccgtc tggtgttacg ttgtagcatg     1020
ccagaaaatt tgtattttca aggggaacct gagcctgaac ctgaaccgga gcccgaacca     1080
gaaccaatgt caaaaggaga ggaactttt actggagtgg ttccaatcct cgtggaactt     1140
gacggcgatg ttaacggtca caagtttagt gtttctggag aaggagaagg ggatgctacg     1200
tacgaaaaac ttacactcaa gttgttgtgt actacgggaa aacttccagt accctggcca     1260
actctagtca ccactctcgg ttatggtgtt cagtgctttg ctcggtatcc tgatcatatg     1320
aaacaacacg acttttcaa atcggcaatg ccggagggtt atgttcagga gaggaccata     1380
tttttcaaag atgatgggaa ttacaaaacc cgagctgaag tcaaattcga aggagatact     1440
ctcgtaaatc gcattgagtt aaagggtatt gactttaaag aggacggcaa catactaggc     1500
cataaacttg agtacaatta caattcacat aatgtgtata taactgctga caaacaaaag     1560
aatggtatta aggctaattt caaaattcgg cacaatattg aagatggtgg tgtacagttg     1620
gcggatcatt accagcaaaa cacacctata ggagatggtc ctgttctatt acctgataat     1680
cactatctct cttatcaatc cgcattgttt aaagacccaa acgagaaag ggatcacatg     1740 gtgcttttgg agtttttgac tgctgctggt attaccgagg ggatgaatga gttatacaaa     1800
gcagatctcc aaaaggacga actttaa                                          1827

<210> SEQ ID NO 31
<211> LENGTH: 2064
<212> TYPE: DNA
<213> ORGANISM: Artificial Sequence
<220> FEATURE:
<223> OTHER INFORMATION: AZ18_2xSP-B (YPet - linker1 - TEV-2xSP-B -
      TEV - linker2 - Ypet) construct

<400> SEQUENCE: 31
atggcttcta aaggagaaga attgttact ggtgtagtgc ctatccttgt tgaattggat       60
ggtgatgtta atggccacaa attctcagta agtggggaag gtgaaggcga cgctacatat     120
ggaaagctca ctcttaagct gctatgtact actggaaagt tgcccgtccc ttggccaaca     180
ttggttacaa cacttggata tgggggttcag tgttttgcaa gatatccaga ccacatgaag     240
caacatgact tcttcaaatc tgctatgcca gagggatatg tccaagaaag gacaatattc     300
ttcaaggatg atggaaatta caagacaaga gctgaggtga agttgaagg cgatacactg     360 gttaacagaa tcgaactaaa gggcattgat ttcaaggaag atggaaatat cttagggcat     420
aagctggagt ataactataa ctctcataat gtttacataa ccgcagacaa gcagaaaaac     480
gggattaagg caaatttcaa gattaggcat aacatcgagg atggaggtgt tcagctggca     540
gaccattatc agcaaaatac accaataggt gatggcccag tcttattgcc tgataaccat     600
tatctctcct atcagagtgc tctctttaag gaccctaacg aaaagagaga tcatatggtc     660
ttacttgagt tcttgactgc agccggaatt accgaaggga tgaacgaact ttacaaggag     720
cccgagccgg agcctgagcc agaaccagag ccagagccgc cgaaaatct ttactttcaa     780 ggtttccccta tcccactgcc ttactgctgg ctttgtcgag cccttatcaa gaggattcaa     840
gcaatgatcc caaaggtgc cttagcagtc gccgtggccc aagtttgcag agtagtgcct     900
cttgttgctg gcggaatttg ccaatgtctt gcagagcgtt acagcgttat tctgttggat     960
actctgttgg gcagaatgct acctcaattg gtgtgccgtc tggtgttacg ttgtagcatg    1020
tttcctattc ctctacccta ctgttggctt tgcagagccc tcatcaaaag gattcaggct    1080
```

```
atgataccaa aaggagcttt agctgtagca gtagctcaag tgtgtagagt cgtccccctt    1140
gttgcagggg gaatttgtca gtgccttgct gagcgttata gtgttatctt gctcgatact    1200
ttacttggtc gtatgttgcc ccaactcgta tgccgattag ttttgaggtg ttctatgcca    1260
gaaaatttgt attttcaagg ggaacctgag cctgaacctg aaccgagcc cgaaccagaa     1320 ccaatgtcaa aaggagagga acttttact ggagtggttc caatcctcgt ggaacttgac     1380
ggcgatgtta acggtcacaa gtttagtgtt tctggagaag agaaggggga tgctacgtac    1440
ggaaaactta cactcaagtt gttgtgtact acgggaaaac ttccagtacc ctggccaact    1500
ctagtcacca ctctcggtta tggtgttcag tgctttgctc ggtatcctga tcatatgaaa    1560
caacacgact ttttcaaatc ggcaatgccg gagggttatg ttcaggagag gaccatattt    1620
ttcaaagatg atgggaatta caaaacccga gctgaagtca aattcgaagg agatactctc    1680
gtaaatcgca ttgagttaaa gggtattgac tttaagagg acggcaacat actaggccat     1740
aaacttgagt acaattacaa ttcacataat gtgtatataa ctgctgacaa acaaaagaat    1800
ggtattaagg ctaatttcaa aattcggcac aatattgaag atggtggtgt acagttggcg    1860
gatcattacc agcaaaacac acctatagga gatggtcctg ttctattacc tgataatcac    1920
tatctctctt atcaatccgc attgtttaaa gacccaaacg agaaagggga tcacatggtg    1980
cttttggagt ttttgactgc tgctggtatt accgagggga tgaatgagtt atacaaagca    2040
gatctccaaa aggacgaact ttaa                                            2064

<210> SEQ ID NO 32
<211> LENGTH: 42
<212> TYPE: DNA
<213> ORGANISM: Artificial Sequence
<220> FEATURE:
<223> OTHER INFORMATION: linker sequence 1

<400> SEQUENCE: 32
gagcccgagc cggagcctga gccagaacca gagccagagc cg                        42

<210> SEQ ID NO 33
<211> LENGTH: 42
<212> TYPE: DNA
<213> ORGANISM: Artificial Sequence
<220> FEATURE:
<223> OTHER INFORMATION: linker sequence 2

<400> SEQUENCE: 33
gaacctgagc ctgaacctga accggagccc gaaccagaac ca                        42

<210> SEQ ID NO 34
<211> LENGTH: 6
<212> TYPE: PRT
<213> ORGANISM: Artificial Sequence
<220> FEATURE:
<223> OTHER INFORMATION: synthetic peptide

<400> SEQUENCE: 34

Ser Glu Lys Asp Glu Leu
1               5

<210> SEQ ID NO 35
<211> LENGTH: 4
<212> TYPE: PRT
<213> ORGANISM: Artificial Sequence
<220> FEATURE:
<223> OTHER INFORMATION: synthetic peptide
```

<400> SEQUENCE: 35

Lys Asp Glu Leu
1

<210> SEQ ID NO 36
<211> LENGTH: 4
<212> TYPE: PRT
<213> ORGANISM: Artificial Sequence
<220> FEATURE:
<223> OTHER INFORMATION: synthetic peptide

<400> SEQUENCE: 36

His Asp Glu Leu
1

<210> SEQ ID NO 37
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 37
ccactgacgt aagggatgac gcacaatcc                                     29

<210> SEQ ID NO 38
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 38 aatatttta tt                                                        12

<210> SEQ ID NO 39
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 39
aatatactag tattatttac taaaaaaaat c                                  31

<210> SEQ ID NO 40
<211> LENGTH: 10
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: 4, 5, 6, 7
<220> FEATURE:
<221> NAME/KEY: misc_feature
<222> LOCATION: (4)..(7)
<223> OTHER INFORMATION: n is a, c, g, or t

<400> SEQUENCE: 40 caannnnatc                                                          10

<210> SEQ ID NO 41
<211> LENGTH: 12
<212> TYPE: DNA
<213> ORGANISM: Artificial Sequence

```
<220> FEATURE:
<223> OTHER INFORMATION: synthetic oligonucleotide

<400> SEQUENCE: 41
kwgtgrwaaw rw                                                        12

<210> SEQ ID NO 42
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 42
tgacacgtgg ca                                                        12

<210> SEQ ID NO 43
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 43
aaattaacca a                                                         11

<210> SEQ ID NO 44
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 44
aacctaacct                                                           10

<210> SEQ ID NO 45
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 45
gataaagatt acttcagata taacaaacgt tac                                 33
```